United States Patent [19]

Ibsen et al.

[11] Patent Number: 4,674,980
[45] Date of Patent: Jun. 23, 1987

[54] DENTAL COMPOSITE AND PORCELAIN REPAIR

[75] Inventors: Robert L. Ibsen; William R. Glace; Patricia A. Jensen, all of Santa Maria, Calif.

[73] Assignee: Den-Mat, Inc., Santa Maria, Calif.

[21] Appl. No.: 534,639

[22] Filed: Sep. 22, 1983

Related U.S. Application Data

[63] Continuation-in-part of Ser. No. 374,315, May 3, 1982, abandoned.

[51] Int. Cl.⁴ .......................... C08F 2/50; C08F 4/40; A61K 6/08; C08L 63/10
[52] U.S. Cl. .................................. 433/228.1; 522/13; 522/14; 522/24; 522/28; 522/77; 522/81; 522/103; 523/115; 523/116
[58] Field of Search ................ 204/159.23; 433/228.1; 522/13, 14, 24, 28; 523/115, 116

[56] References Cited

U.S. PATENT DOCUMENTS

| | | | |
|---|---|---|---|
| 3,629,187 | 12/1971 | Waller | 260/41 R |
| 3,931,678 | 1/1976 | O'Sullivan | 204/159.13 |
| 4,097,994 | 7/1978 | Reaville | 204/159.23 |
| 4,113,593 | 9/1978 | Barzynski | 430/281 |
| 4,117,595 | 10/1978 | Ibsen | 32/8 |
| 4,171,252 | 10/1979 | Fantazier | 204/159.23 |
| 4,222,835 | 9/1980 | Dixon | 204/159.16 |
| 4,247,623 | 1/1981 | Guild | 430/281 |
| 4,286,008 | 8/1981 | Reed | 430/281 |
| 4,289,844 | 9/1981 | Specht | 430/281 |
| 4,343,885 | 8/1982 | Reardon | 430/281 |
| 4,387,153 | 6/1983 | Bonneron | 430/253 |
| 4,407,984 | 10/1983 | Ratcliffe | 523/115 |
| 4,414,275 | 11/1983 | Woods | 428/501 |
| 4,422,891 | 12/1983 | Gonser | 427/54.1 |
| 4,459,193 | 7/1984 | Ratcliffe | 526/208 |
| 4,504,231 | 3/1985 | Koblitz | 523/116 |

FOREIGN PATENT DOCUMENTS

| | | |
|---|---|---|
| 994032 | 7/1976 | Canada . |
| 1032684 | 6/1978 | Canada . |
| 1096988 | 3/1981 | Canada . |
| 1103388 | 6/1981 | Canada . |
| 1109597 | 9/1981 | Canada . |
| 569974 | 6/1945 | United Kingdom . |
| 2027921 | 2/1980 | United Kingdom . |

*Primary Examiner*—John C. Bleutge
*Assistant Examiner*—A. H. Koeckert
*Attorney, Agent, or Firm*—Owen, Wickersham & Erickson

[57] ABSTRACT

A filled-resin composition useful for porcelain repair and as a dental composite and therefore made up of non-toxic materials and a method for repairing porcelain or teeth. The composition comprises a methacrylate functional resin usable in dental composites, powdered filler-colorant therein, at least one photoinitiator for the resin in an amount sufficient to initiate polymerization and complete it in depth within about half a minute when exposed to a visible-light output of at least 5,000 foot candles, the photoinitiator being an exciplex of (1) an carbocyclic ketone or acetal and (2) either ethyl-4-dimethyl amino benzoate or ethyl-2-dimethyl amino benzoate, and at least one accelerator-free peroxide curing agent for the resin in an effective amount for completing polymerization within about one-half hour of any portion of the resin not receiving sufficient light to effectuate complete cure before then. The method comprises mixing the components together under ordinary indoor lighting conditions, emplacing the mixture within a few minutes of the mixing, and curing at least a substantial portion of the emplaced mixture in situ for one half-minute under intense visual-light illumintion of at least 5000 foot-candles. Any resin then uncured by light is cured within the next half hour by the peroxide curing agent.

88 Claims, No Drawings

DENTAL COMPOSITE AND PORCELAIN REPAIR

REFERENCE TO RELATED APPLICATION

This application is a continuation-in-part of application Ser. No. 374,315, filed May 3, 1982, now abandoned.

This invention relates to dental composites and porcelain repair material and to methods for making them.

BACKGROUND OF THE INVENTION

Over the years many dental composites have been introduced, each composite possessing certain physical properties. However, substantially all of these dental composites can be categorized into two main groups, self-cured materials and light-cured materials.

The self-cured composites have involved free radical polymerization initiated by benzoyl peroxide (or another suitable peroxide) and accelerated, typically by a tertiary amine such as N,N,dimethyl-p-toluidine. The curing agents must be stored separately from the resin they are to cure, and they are mixed together just before use.

The light-cured composites have involved free radical polymerization initiated by the photoexcitation of light-sensitive compounds by ultraviolet or visible light. They are single-component systems, typically pastes, stored in opaque containers until the time of cure. Some of the photoinitiators that have been employed are the benzoin ethers, benzil ketals, dialkoxyacetophenones, benzophenones, thioxanthones, and hydroxyalkylphenones.

In the practice of dentistry, some tooth repairs have been better achieved by self-cured composites and some have been better achieved by light-cured composites. While many factors have helped to determine whether a dentist would or should choose a self-cured material or a light-cured material, the prime factors have been working time, setting time, and the architecture of the cavity preparation.

The light-cured composites, combined with special high-lumen lighting units employing fiber optics, have offered variable working times and fast "snap" sets. Setting can take between ten and forty seconds in many instances. However, the use of light-cured composites has been limited by the depth of the repair and the ease of light penetration. Relatively unobstructed, clean, shallow repair surfaces have been required. Visible-light-cured materials have helped in solving some of the limitations caused by repair depth, by roughly doubling the depths at which cure is effective as compared to ultra-violet light-cured material. Also, many dentists have felt more comfortable using a visible, as opposed to an ultra-violet, activating light source.

The amount of cure is variable and is a function of exposure to lumens of visible light. These facts result in extremely dangerous situations in many dental restorations; because most dentists do not realize this deficiency, because light-cured systems are advertised to be able to be cured through tooth structure. In reality, the situation is, at best, a gradient level of cure obtained in relation to the amount of lumens of light energy available to the restorative resin. That is to say, layers close to the light source undergo greater percent polymerization than the underlying layers. Consequently, the incompletely polymerized restoration may wash out leak, or fail in adhesion. Yet the surface or bulk of the restoration may appear clinically adequate, even though new secondary decay may be beginning, and, because of its concealment, result in death of the pulp or loss of the tooth.

When a light-cured resin liner is used with a light-cured paste composite at a depth of around 3 mm. or greater, the resin liner may not cure because of insufficient light reaching the resin. Uncured resin liner can cause leaching, pulpal irritation, and loss of adhesion. Heretofore, the resin liner had, therefore, to be polymerized prior to placement of the composite. With this invention, such double cure is unnecessary.

Self-cured systems have offered assurance of polymerization throughout the polymer mass used in any repair surface architecture. However, their use has been limited by manufacturer-determined work times and set times. The peroxide and the accelerator could be adjusted to give widely varying setting times; the quicker the set time, the quicker the placement had to be made. Thus, in order to give enough time for accurate placement, the set times had to be longer than were desirable. Generally, set times have been at least two or three minutes after mix, and placement has had to be completed within forty-five seconds after mix. This had made dentists work somewhat faster than was desirable for many placements, and even then the patient had to be immobilized longer than was desirable before the composition set.

This invention overcomes the deficiencies of light-cured systems, while preserving their functional benefits. It also overcomes the deficiencies of the self-cured systems by enabling quicker set times coupled with longer placement times, if desired.

The system of this invention thus offers the best properties of both types of curing systems without suffering from the limitations of either, and therefore it significantly advances the practice of dentistry and the science of dental materials.

The system of the present invention can be in a powder-liquid, paste-paste, paste-powder, or gel-powder form, so that there is no loss in versatility of possible embodiments.

Similar problems occur with porcelain repair systems in general, not only in dental uses, but for repairing such porcelain articles as bathtubs, and the invention solves these problems also.

SUMMARY OF THE INVENTION

This invention comprises a composite system combining a small amount of peroxide curing agent, free from accelerator, with certain photoinitiator systems called exciplexes. A two-component system is required, with mixture just before use. Conveniently, the resin and its exciplex members can be stored in opaque (preferably black) containers as one component, with or without some of the filler. The peroxide is stored in a separate component, including much or all of the filler-colorant, in a container which need not be opaque. The two components are mixed just prior to application, and there is a wide latitude of mixing time, because no accelerator is used. The curing effect of the peroxide in the resin is quite slow, while the exposure of the resin and photoinitiator exciplex members in ordinary light —whether daylight or artificial light—will not result in substantial curing. The time for placement is not critical, because neither the photoinitiator exciplex nor the peroxide causes quick curing at this stage. After placement, a high-lumen light source is used with a fiber-optics bundle to effect rapid cure (typically, ten to forty seconds) down to a substantial depth. If the cavity being filled is deeper than that depth, or if some of the placed material has been shaded from the light or not adequately illuminated, the light alone does not effect sufficient cure. However, the cured deposit covering the uncured material holds the uncured material in place, and the peroxide has been found to effect cure of the uncured material in about an hour, and usually in about half that long.

To explain exciplexes: as in photoinitiator systems generally, absorption of light by the ketone group of some photoinitiators results in promotion of the photoinitiator to a chemically reactive excited state; alpha-cleavage results, and free radicals are formed. "In the case of appropriate donor/acceptor systems, interaction between an electronically excited molecule and a ground-state molecule of another type may form an excited-state complex, termed an 'exciplex'." Roffey, C. G., *Photopolymerization of Surface Coatings,* p. 70, John Wiley and Sons, Ltd., New York, 1982.

The incorporation of a suitable peroxide, preferably benzoyl peroxide, with the photoinitiated composite system has a synergistic effect on the free-radical polymerization, resulting in uniform cure without limitation after exposure to the activating light source. The peroxide content is preferably about 0.05% to about 0.3% of the total composition.

The exciplex photoinitiators of this invention rely on a carbocyclic ketone, i.e., an aromatic or alicyclic ketone or acetal and either ethyl-4-dimethyl amino benzoate or ethyl-2-dimethyl amino benzoate. The amount should be enough to initiate polymerization in the selected resin and complete it in depth within about half a minute when the filled-resin composition is exposed to a visible-light output of at least 5,000 foot candles. The peroxide should be present in amount sufficient to complete, within about an hour, the resin's polymerization, where it is not completed by the photoinitiator-derived action, as where the light never reaches the resin in the needed amount.

Suitable photoinitiators for this invention include the following exciplex-forming photoinitiators:

2,3-Bornanedione with ethyl-4-dimethyl amino benzoate
2,3-Bornanedione with ethyl-2-dimethyl amino benzoate
Benzil with ethyl-4-dimethyl amino benzoate
Benzil with ethyl-2-dimethyl amino benzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophenone with ethyl-2-dimethyl amino benzoate
Benzoin methyl ether with ethyl-4-dimethyl amino benzoate
Benzoin methyl ether with ethyl-2-dimethyl amino benzoate.

There are, of course, many other compounds capable of photoinitiation. Many of these are taught in U.S. Pat. No. 4,222,835, to Dixon. However, Dixon's formulations were intended for industrial fabrication, whereas the present invention involves formulations which can be left in the human mouth for many years. Consequently, compounds which are known or are suspected to be toxic, carcinogenic, teratogenic, mutagenic, etc. are not considered.

The present invention provides a much deeper cure than do light-cured composites and obtains a much more uniform degree of cure than do such systems. It obtains a certainty of cure under overhangs, as opposed to prior-art light-cured composites, and a more reliable cure through tooth structure than the prior-art light-cured composites. It provides more uniformity of cure, regardless of exposure time or intensity. It provides better adhesion to the teeth or to substrates such as porcelain as used in dentistry and in plumbing fixtures, apparently due to more complete polymerization. It has a longer shelf-life than self-cured composites. It has better physical properties than most prior-art light-cured composites, especially lower water absorption.

It does not develop color bodies in composites using chemically active glasses, such as strontium glass, where some curing systems do develop objectionable color. Moreover, the composite, when installed and cured in a dental environment, looks like the tooth, not only in ordinary light but also in ultra-violet light. In ultra-violet light it fluoresces to substantially the same degree as the tooth itself.

As stated above, the product is made up of two separate formulations, one containing all or much of the material to be cured along with the exciplex photoinitiators. This formulation is kept from light, as in an opaque container. The other formulation contains the peroxide curing agent, preferably along with any ingredient not itself cured thereby, such as the filler-colorants. In many instances (as in paste-paste systems) it is preferred that the composition be so formulated that equal amounts of the two formulations are mixed together when they are to be used. In powder-liquid systems, there is usually two to three and one-half as much powder as liquid in each mixture.

DESCRIPTION OF SOME PREFERRED EMBODIMENTS

The binders or resins to be cured comprise substantially all of those currently used in dental composites. These are all methacrylate-functional resins. Typical is ethoxylated bisphenol-A-dimethacrylate. Others include Bis-GMA and the adducts disclosed in Waller's U.S. Pat. No. 3,629,187. Mixtures of resins may be used. Waller's adducts are of 2-2'-propane bis[3-(4-phenoxy)-1,2-hydroxy propane-1-methacrylate] and a mono- or di-isocyanate.

The curing agents, as said, are of two types: peroxides and photoinitiators. A suitable and preferred peroxide is benzoyl peroxide. Some other peroxides are either inoperable or have dangerous toxic side effects.

The photoinitiators are ordinarily in the same component as the resin or gel, the resin-(or gel)-photoinitiator exciplex components mixture being kept in opaque containers until use. The peroxide is ordinarily kept separate from the resin, usually with or upon the filler-colorant or most of the filler-colorant. In paste-paste systems, some of the resin may be in the same component as the peroxide.

Suitable exciplex-forming photoinitiators include the following:

2,3-Bornanedione with ethyl-4-dimethyl amino benzoate 2,3-Bornanedione with ethyl-2-dimethyl amino benzoate Benzil with ethyl-4-dimethyl amino benzoate Benzil with ethyl-2-dimethyl amino benzoate 2-Isopropyl thioxanthone with ethyl-4-dimethyl amino benzoate 2-Isopropyl thioxanthone with ethyl-2-dimethyl amino benzoate Dibenzyl ketone with ethyl-4-dimethyl amino benzoate Dibenzyl ketone with ethyl-2-dimethyl amino benzoate 2-Hydroxy-2-methyl-1-phenyl-propane-1-one with ethyl-2-dimethyl amino benzoate 2-Hydroxy-2-methyl-1-phenyl-propane-1-one with ethyl-4-dimethyl amino benzoate Benzil dimethyl acetal with ethyl-4-dimethyl amino benzoate Benzil dimethyl acetal with ethyl-2-dimethyl amino benzoate Dimethoxy acetophenone with ethyl-4-dimethyl amino benzoate Dimethoxy acetophenone with ethyl-2-dimethyl amino benzoate Benzoin methyl ether with ethyl-2-dimethyl amino benzoate Benzoin methyl ether with ethyl-4-dimethyl amino benzoate To the best of our knowledge, no one has previously suggested that the combination of any of these light-curing exciplex photoinitiators with any peroxide could bring about better curing of these dental resins. Likewise, it is not ordinary to utilize peroxide in such small amounts as those utilized in this invention to initiate polymerization of these resins. Furthermore, peroxide curing agents are conventionally employed with accelerators, and no accelerator is used here. Consequently, the results obtained by this invention were totally unexpected.

Practically all inert filler-colorants currently used or usable in dental composites are usable herein. Preferably, they are neither too coarse not too fine. The compositions employed in this invention may contain at least about 10% by weight and up to about 90% by weight, and preferably about 70-80% by weight, of a finely divided, inert inorganic filler-colorant. The filler-colorant, which may be in the form of spheres, platelets, fibers, whiskers, or particles of any regular or irregular shape and which preferably is transparent or translucent, may comprise for example, apatite, soda glass, barium glass, strontium glass, borosilicate glass, silica, fumed silica, flint silica, alumina, quartz, lithium aluminum silicate, or the like. Mixtures of more than one filler-colorant may be used. The particle size of the filler-colorant may range from about 0.005 to about 0.5 microns in the case of microfine silica, to not greater than about 500 microns in the case of irregularly shaped particles. Further, a range of particles sizes may be used. Where the filler-colorant is in the form of fibers, the maximum dimension of the fibers preferably is not greater than about 110 microns. On the other hand, where the filler-colorant is in the form of spheres or platelets or is irregularly shaped, the maximum dimension of the particles preferably is not greater than about 350 microns.

The identity of the filler-colorant is not critical, but barium-containing glass (hereinafter called "barium glass"), strontium-containing glass (hereinafter called "strontium glass"), lithium aluminum silicate, flint silica, and fumed silica are excellent fillers and mixtures of these are usually preferable to the use of just one of them. For example, lithium aluminum silicate has a negative heat coefficient of expansion, giving lower overall thermal dimensional changes to the composite. Barium and strontium glass impart opacity to X-rays. Flint silica imparts tooth-like color, and fumed silica adjusts viscosity and improves polishability.

One example of barium glass is Ray-Sorb T-2000, a product of Kimble Division of Owens-Illinois Glass Company. The same company makes Ray-Sorb T-4000, an example of strontium glass.

Preferably, the peroxide is dispersed on the filler-colorant powder, or by being dissolved in a suitable solvent, is sprayed on the filler-colorant powder, and the solvent evaporated. Preferably, the peroxide is deposited in combination with a silane, such as gamma-methacryloxy propyl trimethoxy silane (sold by Union Carbide as A-174 silane), which is used to improve bonding between the filler and the resin. The benzoyl peroxide and the silane may be dissolved in methylene chloride, chloroform, ether, or acetone, for example. Then a slurry is made with the powdered filler-colorant; the solvent is stripped off, leaving the silane and the peroxide deposited on the dry powder filler-colorant.

Glacial acetic acid is often used, in very small amounts, because the hydrolysis reaction which attaches the silane molecule to the filler-colorant particle is carried out most effectively at a pH slightly less than neutral.

Butylated hydroxytoluene is sometimes used in order to scavenge small amounts of free radicals which can form during extended shelf storage.

The invention can assume several forms: a powder-liquid form, a paste-paste form, a paste-powder form, and a gel-powder form. These forms will be considered in order.

Powder-liquid systems

In general, the powder in this form comprises a suitable filler-colorant material, a suitable silane, such as gamma-methacryloxy propyl trimethoxy silane, and a suitable peroxide curing agent such as benzoyl peroxide. Preferably, these ingredients are in the following approximate range of proportions by weight:

Powder

| Ingredients | Percentage by Weight |
| --- | --- |
| Filler-colorant | 99.85 to 97.70% |
| Silane | 0.10 to 1.55% |
| Peroxide curing agent | 0.05 to 0.70% |
| Glacial acetic acid | 0.00 to 0.05% |

As stated above, the filler-colorant may be a mixture of some or several of the filler-colorants listed above, or it may be just one type of filler.

Liquid

| Ingredients | Percentage by Weight |
| --- | --- |
| Resin | 99.93 to 81.95% |
| Photoinitiator exciplex | 0.7 to 18% |
| Butylated hydroxy toluene | 0.00 to 0.05% |

The formulae may be further generalized in a somewhat more specific manner as follows: it being understood that the various types of ingredients (e.g., filler-colorant, resin, etc.) will be used in quantities that will total to the amounts just spelled out above:

Powder

| Ingredients | Percentage by Weight |
| --- | --- |
| Barium glass | 0 to 30 |
| Lithium aluminum silicate | 0 to 99.85 |
| Flint silica | 0 to 10 |
| Borosilicate glass | 0 to 99.85 |
| Custer feldspar | 0 to 10.00 |
| Fumed synthetic silica | 0 to 99.85 |
| Quartz | 0 to 99.85 |
| Titanium dioxide | 0 to 0.15 |
| Tinting agents (e.g., iron oxides) | 0 to 5 |
| A-174 Silane | 0.1 to 1.55 |
| Peroxide curing agent | 0.05 to 0.70 |
| Glacial acetic acid | 0 to 0.05 |

Liquid

| Ingredients | Percentage by Weight |
| --- | --- |
| Bis-GMA | 0 to 80 |
| Ethoxylated bisphenol-A-dimethacrylate | 0 to 99.3 |
| Ethylene glycol dimethacrylate | 0 to 60 |
| Diethylene glycol dimethacrylate | 0 to 60 |
| Triethylene glycol dimethacrylate | 0 to 60 |
| Polyethylene glycol dimethacrylate | 0 to 60 |
| Photoinitiator (one or more from the exciplex list above) | 0.7 to 18 |
| Butylated hydroxy toluene | 0 to 0.05 |

Tinting agents are used to impart a more toothlike color. Red and yellow iron oxides are usually employed.

Storage life for each mixture is very long, no deterioration having been noticed so far over a period of two and one-half years. The powder and the liquid are mixed together in a ratio of weight from about 1:1 to about 4:1 powder to liquid, just before they are needed. Mixing may be accomplished on a paper mixing pad, with a plastic instrument. Mixing may be done under normal room lighting conditions, as found in the dental operatory, illumination typically varying in intensity from about 80 to about 100 foot candles. Under these conditions, the paste begins to gel after about 10 to 30 minutes, depending on the particular formulations and illuminations.

When it is desired to initiate curing, the mixed material is exposed to the output from a dental visible light curing unit. For all examples cited herein, a Visar curing light, marketed by Den-Mat, Inc., Santa Maria, Calif., was used. This unit utilizes a type EKE or EJV quartz-halogen light bulb, operating at 21 VAC. The light is transmitted to the work site by a flexible fiber-optic bundle, ¼ inch in diameter by four feet in length. Other units are available from other manufacturers. All are similar in principle and results. Results of these examples would be expected to differ only in degree if other units were used. The output of the Visar unit used is $180 \times 10^4$ Candella per square meter, giving illumination of about 20,000 foot candles on the material being cured. Satisfactory operability can be achieved with 5,000 foot candles.

Under these conditions, the material cures in from 10 seconds to 30 seconds, with a cured depth of from 0.60 to 5.60 mm. Upon further standing, that is, from 5 minutes to 35 minutes, the material exhibits a cure depth of greater than 12 mm. It shows a tensile strength, measured by the diametral method on samples 6 mm diameter by 3 mm high, of between 4800 psi and 7000 psi. A popular prior-art, light-cured dental composite, when tested in identical fashion, showed a cured depth of 3.05 mm immediately after exposure to the curing light, but this cure depth did not increase over a period of 16 hours after cure, and its diametral tensile strength was only 2030 psi.

EXAMPLE 1

Powder-Liquid System

Powder

| Ingredients | Percentage by Weight |
| --- | --- |
| Barium glass | 28.63% |
| Lithium aluminum silicate | 67.84% |
| Flint silica | 2.84% |
| Benzoyl peroxide | 0.20% |
| A-174 silane | 0.47% |
| Glacial acetic acid | 0.02% |

A-174 silane is a Union Carbide product, chemically gamma-methacryloxy propyl trimethoxy silane. The barium glass may be Ray-Sorb T-2000, a product of Kimble Division of Owens-Illinois Glass Company or may be barium aluminum silicate.

Liquid

| Ingredients | Percentage by Weight |
| --- | --- |
| Ethoxylated bisphenol-A-dimethacrylate | 95.53% |
| 2,3-Bornanedione | 0.17% |
| Ethyl-4-dimethylamino-benzoate | 4.30% |

The powder and the liquid were mixed together, preferably in a ratio by weight of about 2:1 to about 3½:1, powder to liquid, just before they were needed. Mixing took about twenty seconds. The mixtures are preferably applied within about five minutes. The setting time was about twenty minutes when not exposed to a dental curing light, but was less than thirty seconds on exposure to a dental curing light. The result was a hard filling.

EXAMPLE 2

Powder-Liquid System

Powder

| Ingredients | Percentage by Weight |
| --- | --- |
| Barium glass | 29.82% |
| Lithium aluminum silicate | 68.30% |
| Flint silica | 1.22% |
| $TiO_2$ | 0.02% |
| Benzoyl peroxide | 0.15% |
| A-174 silane | 0.47% |
| Glacial acetic acid | 0.02% |

Liquid

| Ingredients | Percentage by Weight |
| --- | --- |
| Ethoxylated bisphenol-A-dimethacrylate | 91.50% |
| 2,Isopropylthioxanthone | 0.17% |
| Ethyl-4-dimethylamino-benzoate | 8.33% |

The powder and the liquid were mixed together, preferably in a ratio by weight of from about 2:1 to about 3½:1, powder to liquid, just before they were needed. Mixing took about twenty seconds. The mixtures should preferably be applied within about five minutes. The setting time was about twenty minutes when not exposed to a dental curing light, but was less than thirty seconds on exposure to a dental curing light. The reult was a hard filling.

EXAMPLE 3

Hardness comparisons with some prior-art systems

A disk of a commercially available light-curable dental composite was prepared, 20 mm diameter by 1 mm thick. One-half of this disk was shaded with aluminum foil, and the disk then was placed under a photoflood lamp for 15 minutes. The sample was removed from under the lamp, the foil removed from the samples, and Barcol hardness measured on both the shaded and unshaded halves. The unshaded half showed a Barcol hardness of 82, while the shaded side had a Barcol hardness reading of less than 1. This same experiment was performed on two disks made of the mixed but uncured material of each of Examples 1 and 2, and both sides of both disks showed a Barcol hardness of 92.

EXAMPLE 4

Comparison of degree of cure

A series of tests was performed on several commercially-available light-curing composites to determine the degree of cure of the resin matrix. Testing was accomplished by preparing duplicate samples, 1 mm thick by 40 mm in diameter. These samples were cured by exposing them to a photoflood lamp for 30 minutes, and then they were placed in 37° C. water for 24 hours. The samples were then dried, and placed in a desiccator and weighted daily until constant weight (±0.5 mg.) was achieved. The samples were then granulated, placed in a glass thimble and extracted for 12 hours in a Soxhlett extraction apparatus with methylene chloride. After extraction, the samples were weighted and the weight loss converted to percent uncured monomer removed.

When two popular commercially-available light-cured dental composites were tested in this manner, the cured product contained 3.08% and 5.26% extractables, representative of the amount of uncured monomer.

The materials of Examples 1 and 2 of this invention, when tested in the same manner, contained, respectively, only 1.87% and 2.04% extractables, showing a much higher degree of cure.

EXAMPLE 5

Comparison of degree of water sorption

A series of three light-cured dental restoratives were tested in order to determine the degree of water sorption. Samples were in duplicate, and were configured and tested in accordance with American Dental Association Specification No. 27.

Two popular commercially-available light-cured dental restoratives were found to have water sorption values of 1.05 and 0.95 mg/cm$^2$, respectively. The material of Example 1 gave a value of only 0.86 mg/cm$^2$, while that of Example 2 gave a value of only 0.45 mg/cm$^2$.

EXAMPLE 6

Powder-Liquid system of porcelain repair

The powder-liquid system of Example 1 was tested as a porcelain repair material, as described in U.S. Pat. No. 4,117,595.

A commercially available material marketed to practice the above-mentioned patent had test results of 2015 psi bond strength (average of 5 samples) when tested 7 days after preparation, being stored meantime in water at 37° C.

The materials of Examples 1 and 2, when tested in the same fashion, with the same test equipment, gave results of 2400 psi bond strength or 26.6% higher.

EXAMPLE 7

Comparison with a conventional powder-liquid system (using larger amounts of benzoyl peroxide than this system)

Powder

| Ingredients | Percentage by Weight |
| --- | --- |
| Strontium glass (Ray-sorb T-4000) | 95.69% |
| A-174 Silane | 1.44% |
| Benzoyl peroxide | 2.87% |

Liquid

| Ingredients | Percentage by Weight |
| --- | --- |
| Ethoxylated bisphenol-A-dimethacrylate | 77.21% |
| Triethylene glycol dimethacrylate | 19.31% |
| 1-Hydroxy-4-methoxy-benzophenone | 1.93% |
| Butylated hydroxytoluene | 0.05% |
| N,N—2-hydroxyethyl-p-toluidine | 1.50%. |

The powder and liquid were mixed in a weight ratio of 3:1 of powder to liquid and cured properly. However, a bright green color was formed on curing. The mixture was repeated after acid-washing the strontium glass, but the green color persisted. The mixture was again repeated using N,N-3,5-tetramethylaniline as a substitute for the N,N-2-hydroxyethyl-p-toluidine. Again the green color developed.

The mixture was repeated once again using N,N-dimethyl-p-toluidine as activator instead of the N,N-2-hydroxyethyl-p-toluidine. This time the green color did not develop, but the curing characteristics of the composite degraded.

Then the experiment was repeated, using the following powder and liquid:

Powder

| Ingredients | Percentage by Weight |
|---|---|
| Strontium glass (Ray-sorb T-4000) | 98.300% |
| A-174 Silane | 1.475% |
| Benzoyl peroxide | 0.200% |
| Acetic acid | 0.025% |

Liquid

| Ingredients | Percentage by Weight |
|---|---|
| Ethoxylated bisphenol-A-dimethacrylate | 76.41% |
| Triethylene glycol dimethacrylate | 19.10% |
| 2,3-Bornanedione | 0.17% |
| Ethyl 4-dimethyl amino benzoate | 4.30% |
| Butylated hydroxytoluene | 0.02% |

No color developed, the material cured satisfactorily under the output from a Visar dental curing light, and exhibited a depth of cure of 5.20 mm immediately after exposure to the light, and 12 mm depth of cure after 30 minutes. Diametral tensile strength was 6000 psi.

Then the experiment was again repeated, using the liquid of Example 2 with the following powder; parts by weight:

| Ingredients | Percentage by Weight |
|---|---|
| Strontium glass (Ray-sorb T-4000) | 98.23% |
| A-174 Silane | 1.47% |
| Benzoyl peroxide | 0.30% |

No color developed, the material cured satisfactorily under the output from a Visar dental curing light, and exhibited a depth of cure of 3.85 mm immediately after exposure to the light, and 12 mm depth of cure after 30 minutes. Diametral tensile strength ws 5500 psi.

EXAMPLE 8

Powder-Liquid System

Powder

| Ingredients | Percentage by Weight |
|---|---|
| Barium glass | 28.63% |
| Lithium aluminum silicate | 66.80% |
| Flint silica | 2.84% |
| Benzoyl peroxide | 0.20% |
| A-174 silane | 1.51% |
| Glacial acetic acid | 0.02% |

Liquid

| Ingredients | Percentage by Weight |
|---|---|
| Ethoxylated bisphenol-A-dimethacrylate | 95.53% |
| 2,3-Bornanedione | 0.17% |
| Ethyl-4-dimethylamino-benzoate | 4.30% |

Again, the powder and liquid were mixed together in a weight ratios varying from about 2:1 to about 3-1/21, powder to liquid. Curing time was 30 seconds with a depth of 5.50 mm when exposed to a visible light dental curing unit. Diametral tensile strength was 6500 psi. The paste had a workable time of 30 minutes under normal room fluorescent lighting.

EXAMPLE 9

Powder-Liquid System

Powder

| Ingredients | Percentage by Weight |
|---|---|
| Lithium aluminum silicate | 66.80% |
| Barium glass | 28.63% |
| Flint silica | 2.84% |
| Benzoyl peroxide | 0.20% |
| A-174 silane | 1.51% |
| Glacial acetic acid | 0.02% |

Liquid

| Ingredients | Percentage by Weight |
|---|---|
| Bis-GMA, i.e., 2,2'-propane-bis-[3-(4-phenoxy)-1,2-hydroxy propane-1-methacrylate] | 57.40% |
| Triethylene glycol dimethacrylate | 37.94 |
| 2,3-Bornanedione | 0.02% |
| Ethyl-4-dimethylamino-benzoate | 4.64% |

Three parts of the powder and one part of the liquid were mixed together to form a paste. This paste, when exposed to a visible light dental curing unit for 30 seconds, cured to a depth of 5.40 mm. Under normal room fluorescent lighting, the paste had a workable time of approximately 20 minutes. The diametral tensile strength was 6900 psi.

EXAMPLE 10

Powder-Liquid System

Powder

| Ingredients | Percentage by Weight |
|---|---|
| Lithium aluminum silicate | 66.80% |
| Barium glass | 28.63% |
| Flint silica | 2.84% |
| Benzoyl peroxide | 0.20% |
| A-174 silane | 1.51% |
| Glacial acetic acid | 0.02% |

Liquid

| Ingredients | Percentage by Weight |
| --- | --- |
| Ethoxylated bisphenol-A-dimethacrylate | 75.98% |
| Triethylene glycol dimethacrylate | 19.36% |
| 2,3-Bornanedione | 0.02% |
| Ethyl-4-dimethylamino-benzoate | 4.64% |

Three parts of the powder and one part of the liquid were mixed together to form a paste. This paste, when exposed to the output from a Visar dental visible light curing unit for 30 seconds, cured to a depth of 5.30 mm. When left exposed to room fluorescent lighting, the paste had a working time of about 40 minutes and a diametral tensile strength of 6940 psi.

EXAMPLE 11

Powder-Liquid System

Powder

| Ingredients | Percentage by Weight |
| --- | --- |
| Barium glass | 26.66% |
| Lithium aluminum silicate | 62.24% |
| Flint silica | 9.01% |
| Benzoyl peroxide | 0.60% |
| A-174 silane | 1.47% |
| Glacial acetic acid | 0.02% |

Liquid

| Ingredients | Percentage by Weight |
| --- | --- |
| Ethoxylated bisphenol-A-dimethacrylate | 91.50% |
| 2-Isopropyl thioxanthone | 0.17% |
| Ethyl-4-dimethylamino-benzoate | 8.33% |

The powder and liquid were mixed together in a weight ratio varying from about 2:1 to about 3½:1, powder to liquid. Mixing, working, and curing times were about the same as in Example 1.

EXAMPLE 12

Powder-Liquid System

Powder

| Ingredients | Percentage by Weight |
| --- | --- |
| Lithium aluminum silicate | 69.78% |
| Barium glass | 29.90% |
| Benzoyl peroxide | 0.30% |
| Glacial acetic acid | 0.02% |

Liquid

| Ingredients | Percentage by Weight |
| --- | --- |
| Bis-GMA, i.e., 2,2'-propane-bis-[3-(4-phenoxy)-1,2-hydroxy propane-1-methacrylate] | 54.6% |
| Triethylene glycol dimethacrylate | 36.4 |
| 2-Isopropyl thioxanthone | 0.02% |
| Ethyl-4-dimethylamino-benzoate | 8.98% |

Three parts of the powder and one part of the liquid were mixed together to form a paste. This paste, when exposed to a visible light dental curing unit for 10 seconds, cured to a depth of 4.79 m when measured at 10 minutes. Under normal room fluorescent lighting, the paste had a workable time of approximately 25 minutes.

EXAMPLE 13

Powder-Liquid System

Powder

| Ingredients | Percentage by Weight |
| --- | --- |
| Lithium aluminum silicate | 69.78% |
| Barium glass | 29.90% |
| Benzoyl peroxide | 0.30% |
| Glacial acetic acid | 0.02% |

Liquid

| Ingredients | Percentage by Weight |
| --- | --- |
| Ethoxylated bisphenol-A-dimethacrylate | 72.80% |
| Triethylene glycol dimethacrylate | 18.20% |
| 2-Isopropyl thioxanthone | 0.02% |
| Ethyl-4-dimethylamino-benzoate | 8.98% |

Three parts of the powder were mixed with one part of the liquid and mixed together to form a paste. This paste, when exposed to the output from a Visar dental visible light curing unit for 30 seconds, cured to a depth of 4.97 mm when measured after 10 minutes. When left exposed to room fluorescent lighting, the path had a working time of about 25 minutes.

EXAMPLE 14

A comparison of curing of various powder/liquid systems utilizing different exciplex-forming photo-initiators A series of thirty resin blends was prepared, all as indicated below as resins A-Z and ZA-ZD, where all the percentages of ingredients are given by weight. Also a standard blend of powder was prepared. Benzoyl peroxide was added to the powder in different levels. The resultant powders were mixed with the resin blends and exposed to the output from a Visar dental curing light for 30 seconds, and the depth of cure measurement was taken.

As controls resin blends were made without one or all of the exciplex members.

On some of these samples, glass tubes 12 mm long were filled with the test material, and were wrapped with black vinyl tape to exclude light for 30 seconds, then the time was measured until the material at the opposite end of the tube was cured. This test will be referred to as the "Infinite Depth of Cure Test" in the following text.

As a control, a popular commercially available light-cured composite was tested in the same manner. It initially cured in 30 seconds to a depth of 3.05 mm, and there was no increase in cure depth when measured after 16 hours.

Standard Blend of Powder

Barium glass: 29.54%,
Lithium aluminum silicate: 68.96%,
A-174 silane: 1.48%
Glacial acetic acid: 0.02%.

Resin A

Ethoxylated bisphenol-A-dimethacrylate: 100.00%.
Resin A was mixed in a ratio of 1:2 with a powder blend containing 0.61% added benzoyl peroxide. No cure was observed.

Resin B

Ethoxylated bisphenol-A-dimethacrylate: 91.50%,
2-Isopropyl thioxanthone: 0.17%,
Ethyl-4-dimethylaminobenzoate: 8.33%.
Resin B was mixed in a ratio of 1:2 with powder blends containing 0.00, 0.15, 0.22, 0.24, 0.26, 0.30, 0.61, and 0.76% added benzoyl peroxide. The following cure depths were observed: 2.55, 3.14, 3.18, 3.30, 3.20, 3.10, 3.68, and 4.90 mm. Resin B was mixed in a ratio of 1:3 with powder blends containing 0.15, 0.22, 0.30, 0.40, and 0.61% added benzoyl peroxide. The following cure depths were observed: 3.05, 3.15, 3.80, 3.20, and 4.80 mm. The time in minutes after light exposure for "infinite cure" of the 1:3 ratio mixed blends were as follows: 20, 15, 15, 10, and 5.

Resin C

Ethoxylated bisphenol-A-dimethacrylate: 91.50%,
2-Isopropyl thioxanthone: 0.17%,
Ethyl-2-dimethylaminobenzoate: 8.33%.
Resin C was mixed in a ratio of 1:2 with powder blends containing 0.00 and 0.61% added benzoyl peroxide. The cure depths observed were 2.15 and 3.05 mm. The time in minutes after light exposure for "infinite cure" of the blend made with the 0.61% added peroxide powder was 15.

Resin D

Ethoxylated bisphenol-A-dimethacrylate: 84.59%,
Dimethoxy acetophenone: 7.70%,
Ethyl-4-dimethylaminobenzoate: 7.71%.
Resin D was mixed in a ratio of 1:2 with powder blends containing 0.00 and 0.61% added benzoyl peroxide. The cure depths observed were 2.65 and 4.95 mm. The time in minutes after light exposure for "infinite cure" of the blend made with the 0.61% added peroxide powder was 9.

Resin E

Ethoxylated bisphenol-A-dimethacrylate: 84.59%,
Dimethoxyacetophenone: 7.70%,
Ethyl-2-dimethylaminobenzoate: 7.71%.
Resin E was mixed in a ratio of 1:2 with powder blends containing 0.00 and 0.61% added benzoyl peroxide. The cure depths observed were 1.60 and 2.35 mm. The time in minutes after light exposure for "infinite cure" of the blend made with the 0.61% added peroxide powder was 15.

Resin F

Ethoxylated bisphenol-A-dimethacrylate: 85.92,
Benzil dimethylacetal: 6.26%,
Ethyl-4-dimethylaminobenzoate: 7.82%.
Resin F was mixed in a ratio of 1:2 with powder blends containing 0.00 and 0.61% added benzoyl peroxide. The cure depths observed were 2.50 and 3.35 mm. The time in minutes after light exposure for "infinite cure" of the blend made with the 0.61% added peroxide powder was 10.

Resin G

Ethoxylated bisphenol-A-dimethacrylate: 85.92%
Benzil dimethylacetal: 6.26%,
Ethyl-2-dimethylaminobenzoate: 7.82%.
Resin G was mixed in a ratio of 1:2 with powder blends containing 0.00 and 0.61% added benzoyl peroxide. The cure depths observed were 1.45 and 2.60 mm. The time in minutes after light exposure for "infinite cure" of the blend made with the 0.61% added peroxide powder was 29.

Resin H

Ethoxylated bisphenol-A-dimethacrylate: 84.59%,
2-Hydroxy-2-methyl-1-phenylpropan-1-one: 7.70%,
Ethyl-2-dimethylaminobenzoate: 7.71%.
Resin H was mixed in a ratio of 1:2 with powder blends containing 0.00 and 0.61% added benzoyl peroxide. The cure depths observed were 0.45 and 1.80 mm. The time in minutes after light exposure for "infinite cure" of the blend made with the 0.61% added peroxide powder was 15.

Resin I

Ethoxylated bisphenol-A-dimethacrylate: 84.59%,
2-Hydroxy-2-methyl-1-phenylpropan-1-one: 7.70%,
Ethyl-4-dimethylaminiobenzoate: 7.71%.
Resin I was mixed in a ratio of 1:2 with powder blends containing 0.00 and 0.61% added benzoyl peroxide. The cure depths observed were 0.95 and 2.55 mm. The time in minutes after light exposure for "infinite cure" of the blend made with the 0.61% added peroxide powder was 8.

Resin J

Ethoxylated bisphenol-A-dimethacrylate: 91.65%,
2-Hydroxy-2-methyl-1-phenylpropan-1-one: 8.35%.
Resin J was mixed in a ratio of 1:2 with powder blends containing 0.00 and 0.61% added benzoyl peroxide. The cure depths observed for viable light were 0.00 and 0.60 mm, and there was no later increase in depth.

Resin K

Ethoxylated bisphenol-A-dimethacrylate: 91.65%,
Dimethoxyacetophenone: 8.35%.
Resin K was mixed in a ratio of 1:2 with powder blends containing 0.00 and 0.61% added benzoyl peroxide. The cure depths observed for variable light were 0.00 and 1.50 mm, and there was no later increase in depth.

Resin L

Ethoxylated bisphenol-A-dimethacrylate: 91.65%,
Benzil dimethylacetal: 8.35%.
Resin L was mixed in a ratio of 1:2 with powder blends containing 0.00 and 0.61% added benzoyl peroxide. The cure depths observed were 1.49 and 1.55 mm for variable light, and there was no subsequent cure.

Resin M

Ethoxylated bisphenol-A-dimethacrylate: 91.65%,
Ethyl-4-dimethylaminobenzoate: 8.35%.
Resin M was mixed in a ratio of 1:2 with powder blends containing 0.00 and 0.61% added benzoyl peroxide. The cure depths observed were 0.00 and 1.45 mm for visible light, and there was no subsequent cure.

Resin N

Ethoxylated bisphenol-A-dimethacrylate: 99.82%,
2-Isopropyl thioxanthone: 0.18%.
Resin N was mixed in a ratio of 1:2 with powder blends containing 0.00 and 0.61% added benzoyl peroxide. The cure depths observed were 0.00 and 1.19 mm for visible light, and there was no subsequent increase in depth of cure.

Resin O

Ethoxylated bisphenol-A-dimethacrylate: 95.53%,
2,3-Bornanedione: 0.17%,
Ethyl-4-dimethylaminobenzoate: 4.30%.
Resin O was mixed in a ratio of 1:3 with powder blends containing 0.20 and 0.22% added benzoyl peroxide. The cure depths observed were both 5.50 mm. The time in minutes after light exposure for "infinite cure" of the blend made with the 0.22% added peroxide was 30.

Resin P

Ethoxylated bisphenol-A-dimethacrylate: 91.70%,
Benzoin methyl ether: 8.30%.
Resin P was mixed in a ratio of 1:3 with a powder blend containing 0.20% added benzoyl peroxide. The cure depth was 1.32 mm. There was no subsequent increase in cure depth.

Resin Q

Ethoxylated bisphenol-A-dimethacrylate: 84.60%,
Benzoin methyl ether: 7.70%,
Ethyl-4-dimethylaminobenzoate: 7.70%.
Resin Q was mixed in a ratio of 1:3 with a powder blend containing 0.20% added benzoyl peroxide. The cure depth was 2.55 mm. The time in minutes after light exposure for "infinite cure" of the blend was 60.

Resin R

Ethoxylated bisphenol-A-dimethacrylate: 82.30%,
Benzoin methyl ether: 7.70%,
Ethyl-2-dimethylaminobenzoate: 10.00.
Resin R was mixed in a ratio of 1:3 with a powder blend containing 0.20% added benzoyl peroxide. The cure depth was 2.65 mm. The time in minutes after light exposure for "infinite cure" of the blend was 45.

Resin S

Ethoxylated bisphenol-A-dimethacrylate: 86.60%,
Benzoin methyl ether: 3.40%,
Ethyl-2-dimethylaminobenzoate: 10.00.
Resin S was mixed in a ratio of 1:3 with a powder blend containing 0.20% added benzoyl peroxide. The cure depth was 2.74 mm. The time in minutes after light exposure for "infinite cure" of the blend was 60.

Resin T

Ethoxylated bisphenol-A-dimethacrylate: 88.80%,
Benzoin methyl ether: 3.50%,
Ethyl-4-dimethylaminobenzoate: 7.70%.
Resin T was mixed in a ratio of 1:3 with a powder blend containing 0.20% added benzoyl peroxide. The cure depth was 3.53 mm. The time in minutes after light exposure for "infinite cure" of the blend was 50.

Resin U

Ethoxylated bisphenol-A-dimethacrylate: 91.70%,
Benzil: 8.30%.
Resin U was mixed in a ratio of 1:3 with a powder blend containing 0.20% added benzoyl peroxide. The cure depth was 4.06 mm. There was no subsequent increase in the depth of cure.

Resin V

Ethoxylated bisphenol-A-dimethacrylate: 84.60%,
Benzil: 7.70%,
Ethyl-4-dimethylaminobenzoate: 7.70%.
Resin V was mixed in a ratio of 1:3 with a powder blend containing 0.20% added benzoyl peroxide. The cure depth was 4.84 mm. The time in minutes after light exposure for "infinite cure" of the blend was 25.

Resin W

Ethoxylated bisphenol-A-dimethacrylate: 84.60%,
Benzil: 7.70%,
Ethyl-2-dimethylaminobenzoate: 7.70%.
Resin W was mixed in a ratio of 1:3 with a powder blend containing 0.20% added benzoyl peroxide. The cure depth was 5.02 mm. The time in minutes after light exposure for "infinite cure" of the blend was 25.

Resin X

Ethoxylated bisphenol-A-dimethacrylate: 91.70%,
Isopropyl benzoin methyl ether: 8.30%.
Resin X was mixed in a ratio of 1:3 with a powder blend containing 0.20% added benzoyl peroxide. The cure depth was 0.90 mm. There was no change in cure depth afterwards.

Resin Y

Ethoxylated bisphenol-A-dimethacrylate: 84.60%,
Isopropyl benzoin methyl ether: 7.70%,
Ethyl-2-dimethylaminobenzoate: 7.70%.
Resin Y was mixed in a ratio of 1:3 with a powder blend containing 0.20% added benzoyl peroxide. The cure depth was 3.33 mm. The time in minutes after light exposure for "infinite cure" of the blend was 90.

Resin Z

Ethoxylated bisphenol-A-dimethacrylate: 84.60%,
Isopropyl benzoin methyl ether: 7.70%,
Ethyl-4-dimethylaminobenzoate: 7.70%.
Resin Z was mixed in a ratio of 1:3 with a powder blend containing 0.20% added benzoyl peroxide. The cure depth was 3.30 mm. The time in minutes after light exposure for "infinite cure" of the blend was 40.

Resin ZA

Ethoxylated bisphenol-A-dimethacrylate: 91.50%,
2,3-Bornanedione: 0.17%,
Ethyl-2-dimethylaminobenzoate: 8.33%.
Resin ZA was mixed in a ratio of 1:3 with a powder blend containing 0.20% added benzoyl peroxide. The cure depth was 5.56 mm. The time in minutes after light exposure for "infinite cure" of the blend was 60.

Resin ZB

Ethoxylated bisphenol-A-dimethacrylate: 88.80%,

Dibenzyl ketone: 3.40,
Ethyl-4-dimethylaminobenzoate: 7.80%.

Resin ZB was mixed in a ratio of 1:3 with a powder blend containing 0.20% added benzoyl peroxide. The cure depth was 1.87 mm. The time in minutes after light exposure for "infinite cure" of the blend was 45 minutes.

Resin ZC

Ethoxylated bisphenol-A-dimethacrylate: 86.60%,
Dibenzyl ketone: 3.40%,
Ethyl-2-dimethyaminobenzoate: 10.00%.

Resin ZC was mixed in a ratio of 1:3 with a powder blend containing 0.20% added benzoyl peroxide. The cure depth was 0.84 mm. The time in minutes after light exposure for "infinite cure" of the blend was 50 minutes.

Resin ZD

Ethoxylated bisphenol-A-dimethacrylate: 96.60%,
Dibenzyl ketone: 3.40%.

Resin ZD was mixed in a ratio of 1:3 with a powder blend containing 0.20% added benzoyl peroxide. The cure depth was 1.55 mm. The time in minutes after light exposure for "infinite cure" of the blend was 52 minutes.

Paste-Paste Systems

Some dentists (and perhaps other users) prefer to work with pastes: most of these users also prefer to use equal amounts of the two pastes, so that paste-paste systems are usually formulated to enable use of equal amounts.

In general, the paste-paste system of the present invention may be formulated as follows:

Paste A

| Ingredients | Percentage by Weight |
| --- | --- |
| Resin | 14 to 39.63 |
| Filler-colorant | 84.68 to 59.46 |
| Peroxide | 0.10 to 0.75 |
| A-174 silane | 1.21 to 0.06 |
| Butylated hydroxytoluene | 0.01 to 0.10 |

Paste B

| Ingredients | Percentage by Weight |
| --- | --- |
| Resin | 14 to 35.43 |
| Filler-colorant | 83.24 to 53.17 |
| Exciplex forming photoinitiator | 1.5 to 3.5 |
| A-174 silane | 1.21 to 0.05 |
| Glacial acetic acid | 0.05 to 0.01 |

The two pastes are preferably mixed in equal amounts. Mixing time, working time, and setting time are approximately the same as for the powder-liquid systems, described above, and the results in cure and hardness are approximately the same, too. Again, ordinary room lighting has little curing effect. The resin may be the same in both pastes, as may the filler. The silane is preferably deposited on the filler of both pastes prior to making the pastes. The presence of both resin and peroxide in Paste A seems not to effect a cure nor to affect substantially the storage life.

More specifically considered, the paste-paste system employs the following formulations:

Paste A

| Ingredients | Percent by Weight |
| --- | --- |
| Bis-GMA | 0 to 32 |
| Ethoxylated bisphenol-A-dimethacrylate | 0 to 40 |
| Ethylene glycol dimethacrylate | 0 to 24 |
| Diethylene glycol dimethacrylate | 0 to 24 |
| Triethylene glycol dimethacrylate | 0 to 24 |
| Polyethylene glycol dimethacrylate | 0 to 24 |
| Barium glass | 0 to 25 |
| Lithium aluminum silicate | 0 to 85 |
| Flint silica | 0 to 8.5 |
| Borosilicate glass | 0 to 85 |
| Fumed synthetic silica | 0 to 52 |
| Quartz | 0 to 85 |
| Strontium glass | 0 to 85 |
| Titanium dioxide | 0 to 0.13 |
| Tinting agents (e.g., iron oxides) | 0 to 4 |
| A-174 Silane | 0.06 to 1.21 |
| Peroxide curing agent | 0.10 to 0.75 |
| Butylated hydroxy toluene | 0.01 to 0.1 |

Paste B

| Ingredients | Percent by Weight |
| --- | --- |
| Bis-GMA | 0 to 32 |
| Ethoxylated bisphenol-A-dimethacrylate | 0 to 40 |
| Ethylene glycol dimethacrylate | 0 to 24 |
| Diethylene glycol dimethacrylate | 0 to 24 |
| Triethylene glycol dimethacrylate | 0 to 24 |
| Polyethylene glycol dimethacrylate | 0 to 24 |
| Barium glass | 0 to 25 |
| Lithium aluminum silicate | 0 to 85 |
| Flint silica | 0 to 8.5 |
| Borosilicate glass | 0 to 85 |
| Fumed synthetic silica | 0 to 52 |
| Quartz | 0 to 85 |
| Strontium glass | 0 to 85 |
| Titanium dioxide | 0 to 0.13 |
| Tinting agents (e.g., iron oxides) | 0 to 4 |
| A-174 Silane | 0.05 to 1.21 |
| Exciplex-forming-photoinitiator | 1.5 to 3.5 |
| Glacial acetic acid | 0.01 to 0.05 |

This formulation should be read with the more general one preceding it, to supply the percentages of fillers, resins, and silane needed, along with appropriate amounts of the curing agents. All percentages are by weight.

EXAMPLE 15

Paste-Paste System

Paste A

| Ingredients | Percentage by Weight |
| --- | --- |
| Ethoxylated bisphenol-A-dimethacrylate | 17.66% |
| Benzoyl peroxide | 0.30% |
| Butylated hydroxytoluene | 0.04% |
| Barium glass | 24.25% |
| Lithium aluminum silicate | 56.43% |
| Fumed silica | 0.92% |
| A-174 silane | 0.40% |

The fumed silica may be Aerosil 200 of Degussa Corp. of Teterboro, N.J.

Paste B

| Ingredients | Percentage by Weight |
| --- | --- |
| Ethoxylated bisphenol-A-dimethacrylate | 14.94% |
| 2,3-Bornanedione | 0.06% |
| Ethyl-4-dimethylamino benzoate | 1.55% |
| Barium glass | 24.394% |
| Lithium aluminium silicate | 56.92% |
| Fumed silica | 0.92% |
| A-174 silane | 1.2% |
| Glacial acetic acid | 0.016% |

The two pastes are preferably mixed in equal quantities just before application and are cured by a dental curing light, such as Visar, or equivalent. When so mixed and exposed to a visible light curing unit for 30 seconds, the material cured to a depth of 5.43 mm. The diametral tensile strength was 6990 psi.

EXAMPLE 16

Paste A

| Ingredients | Percentage by Weight |
| --- | --- |
| Ethoxylated bisphenol-A-dimethacrylate | 17.66% |
| Benzoyl peroxide | 0.30% |
| Butylated hydroxytoluene | 0.04% |
| Strontium glass | 79.88% |
| Fumed silica | 0.92% |
| A-174 silane | 1.20% |

The strontium glass may be Ray-sorb T-4000 of Kimble Division of Owens-Illinois.

Paste B

| Ingredients | Percentage by Weight |
| --- | --- |
| Ethoxylated bisphenol-A-dimethacrylate | 14.94% |
| 2,3-Bornanedione | 0.06% |
| Ethyl-4-dimethylamino benzoate | 1.55% |
| Strontium glass | 81.3284% |
| Fumed silica | 0.92% |
| A-174 silane | 1.20% |
| Glacial acetic acid | 0.0016% |

Equal or substantially equal amounts of pastes A and B are mixed together just before use. When so mixed and exposed to a visible light curing unit for 30 seconds, the material cured to a depth of 5.50 mm. The diametral tensile strength was 4790 psi.

EXAMPLE 17

The pastes from Examples 15 and 16, mixed in equal parts, were exposed to the output from a Visar dental curing unit for 30 seconds. The samples were tested to determine the time required to achieve a 12 mm (or "infinite") depth of cure. The samples were tested as described previously. Pastes A and B of Example 15 when mixed together obtained "infinite" cure in 35 minutes. Pastes A and B of examples 16 when mixed together obtained "infinite" cure in 35 minutes.

EXAMPLE 18

Paste-Paste System

Paste A:

| Ingredients | Percentage by Weight |
| --- | --- |
| Ethoxylated bisphenol-A-dimethacrylate | 17.86% |
| Benzoyl peroxide | 0.10% |
| Butylated hydroxytoluene | 0.04% |
| Barium glass | 24.25% |
| Lithium aluminum silicate | 56.43% |
| Fumed silica | 0.92% |
| A-174 silane | 0.40% |

The fumed silica may be Aerosil 200 of Degussa Corp. of Teterboro, N.J.

Paste B

| Ingredients | Percentage by Weight |
| --- | --- |
| Ethoxylated bisphenol-A-dimethacrylate | 14.94% |
| 2-Isopropyl thioxanthone | 0.06% |
| Ethyl 4-dimethylamino benzoate | 3.00% |
| Barium glass | 23.95% |
| Lithium aluminum silicate | 55.91% |
| Fumed silica | 0.92% |
| A-174 silane | 1.20% |
| Glacial acetic acid | 0.02% |

The two pastes are preferably mixed in equal quantities just before application and are cured by a dental curing light, such as Visar, or equivalent.

EXAMPLE 19

Paste-Paste System

Paste A

| Ingredients | Percentage by Weight |
| --- | --- |
| Ethoxylated bisphenol-A-dimethacrylate | 17.36% |
| Benzoyl peroxide | 0.60% |
| Butylated hydroxytoluene | 0.04% |
| Strontium glass | 79.88% |
| Fumed silica | 0.92% |
| A-174 silane | 1.20% |

The strontium glass may be Ray-sorb T-4000 of Kimble division of Owens-Illinois.

Paste B

| Ingredients | Percentage by Weight |
| --- | --- |
| Ethoxylated bisphenol-A-dimethacrylate | 14.94% |
| 2-Isopropyl thioxanthone | 0.06% |
| Ethyl-4-dimethylamino benzoate | 3.00% |
| Strontium glass | 79.864% |
| Fumed silica | 0.92% |
| A-174 silane | 1.20% |
| Glacial acetic acid | 0.016% |

Equal or substantially equal amounts of pastes A and B are mixed together just before use.

EXAMPLE 20

A series of seven pastes was made up as shown in Table I, all percentages being by weight. Pastes P, Q, and R contained light-activated curatives, and no peroxide. Pastes S, T, U, and V contained peroxide and no light-activated curatives. These materials were mixed in equal parts, according to the plan shown in Table II. The resultant mixed pastes were exposed to the output from a Visar dental curing unit for 30 seconds, and the depth of cure was measured. The results were shown in Table II. the samples were further tested (as described previously) to determine the time required to achieve a 12 mm (or "infinite") depth of cure. These results are shown in Table III.

TABLE I

Paste Embodiment Key
For Paste-Paste Charts

| Ingredients | Percentage by Weight |
|---|---|
| Paste P: | |
| Ethoxylated bisphenol-A-dimethacrylate | 16.07% |
| 2-Isopropyl thioxanthone | 0.03% |
| Ethyl-4-dimethylamino benzoate | 1.49% |
| Barium glass | 24.056% |
| Lithium aluminum silicate | 56.244% |
| A-174 silane | 1.19% |
| Glacial acetic acid | .02% |
| Aerosil 972 | .90% |
| Paste Q: | |
| Ethoxylated bisphenol-A-dimethacrylate | 16.44% |
| 2-Isopropyl thioxanthone | 0.015% |
| Ethyl-4-dimethylamino benzoate | 1.52% |
| Titanium dioxide | .05% |
| Aerosil 972 | .92% |
| Barium glass | 23.957% |
| Lithium aluminum silicate | 55.899% |
| A-174 silane | 1.18% |
| Glacial acetic acid | 0.019% |
| Paste R: | |
| Ethoxylated bisphenol-A-dimethacrylate | 14.83% |
| 2-Isopropyl thioxanthone | 0.054% |
| Ethyl-4-dimethylamino benzoate | 2.706% |
| Barium glass | 24.056% |
| Lithium aluminum silicate | 56.244% |
| A-174 silane | 1.19% |
| Glacial acetic acid | 0.02% |
| Aerosil 972 (fumed silica) | 0.90% |
| Paste S: | |
| Ethoxylated bisphenol-A-dimethacrylate | 17.75% |
| Butylated hydroxytoluene | .066% |
| Benzoyl peroxide | .24% |
| Aerosil (fumed silica) | .92% |
| A-174 silane | .41% |
| Barium glass | 24.10% |
| Lithium aluminum silicate | 56.514% |
| Paste T: | |
| Ethoxylated bisphenol-A-dimethacrylate | 19.61% |
| Aerosil (fumed silica) | .90% |
| Benzoyl peroxide | .98% |
| Barium glass | 23.20% |
| Lithium aluminum silicate | 54.13% |
| A-174 silane | 1.16% |
| Glacial acetic acid | 0.02% |
| Paste U: | |
| Ethoxylated bisphenol-A-dimethacrylate | 18.00% |
| Aerosil (fumed silica) | .92% |
| Benzoyl peroxide | .74% |
| Barium glass | 24.72% |
| Lithium aluminum silicate | 54.413% |
| A-174 silane | 1.19% |
| Glacial acetic acid | .017% |
| Paste V: | |
| Ethoxylated bisphenol-A-dimethacrylate | 16.42% |
| Aerosil (fumed silica) | .92% |
| Benzoyl peroxide | .72% |
| Barium glass | 24.10% |
| Lithium aluminum silicate | 57.364% |
| A-174 silane | .41% |
| Butylated hydroxytoluene | .066% |

In the above paste-paste examples, it must be born in mind that the peroxide content of the total mixed system was only about half that shown in the formulation, as the two pastes were mixed together at a 1:1 ratio and one paste had no peroxide at all.

TABLE II

Paste-Paste Systems
Depth (in mm) of cure
Immediately after 30 second light exposure

| Paste Containing Light Curatives | Paste Containing BPO** in Resin | Paste Containing BPO** on Powder | Depth |
|---|---|---|---|
| P* | | | 4.50 |
| Q | | | 2.85 |
| P | S | | 2.95 |
| R | | T | 4.80 |
| P | | T | 5.15 |
| P | | U | 5.04 |
| R | | U | 5.15 |
| P | V | | 2.65 |
| R | V | | 3.75 |

*See Key to Paste Embodiments
**BPO—Benzoyl peroxide

TABLE III

Paste-Paste Systems
Time (in min) After Light Exposure to
Obtain "Infinite" Depth of Cure

| Paste Containing Light Curatives | Paste Containing BPO** in Resin | Paste Containing BPO** on Powder | Depth |
|---|---|---|---|
| P* | | | N/A |
| Q | | | N/A |
| P | S | | 20 |
| R | | T | 3 |
| P | | T | 4 |
| P | | U | 4 |
| R | | U | 4 |
| P | V | | 18 |
| R | V | | 7 |

*See Key to Paste Embodiments
**BPO—Benzoyl peroxide

Paste-Powder Systems

A third type of system is somewhat of a blend between the powder-liquid system and the paste-paste system. Here, the powder remains substantially the same as in the powder-liquid system, except that it has a larger percentage of peroxide. However, the paste contains the exciplex-forming members dissolved in a liquid resin, and the filler, suspended therein. This paste material should be stored in a light-free container. Typically, a black polyethylene or polypropylene syringe may be used as the container, as in the paste-paste systems.

The powder is coated with a suitable silane, such as gamma methacryloxy propyl trimethoxy silane, and has benzoyl peroxide dispersed over its surface. This component may be stored in a container suited to dispersing small amounts. A small cylindrical plastic vial with a small orificed dropper tip is preferred.

In practice, an amount of the paste is expressed onto a mixing pad, then a very small amount—1/10 to 1/20—of the powder is mixed in; so the powder has more peroxide in it than in previous systems discussed. The result is that the paste is thickened—a condition desired by some dentists—and also that depth of cure and cure efficiency are improved.

A general formulation may be expressed as follows:

Paste

| Ingredients | Percentage by Weight |
|---|---|
| Resin | 13.00 to 63.4 |
| Filler-colorant | 84.78 to 32.85 |
| Exciplex-forming photoinitiators | 0.7 to 3.696 |
| A-174 silane | 1.50 to 0.05 |
| Glacial acetic acid | 0.02 to 0.004 |

Powder

| Ingredients | Percentage by Weight |
|---|---|
| Filler-colorant | 99.58 to 83.83 |
| A-174 silane | 0.10 to 6 |
| Peroxide | 0.30 to 10.00 |
| Glacial acetic acid | 0.02 to 0.17 |

The mixture is preferably done in a ratio varying between 20 to 1 of paste to powder to 10 to 1 of paste to powder. More specifically, this system may comprise the following, with resin, filler, etc., ingredients always lying within the above-given ranges and percentages being by weight:

Paste

| Ingredients | Percent by Weight |
|---|---|
| Bis-GMA | 0 to 32 |
| Ethoxylated bisphenol-A-dimethacrylate | 0 to 63.4 |
| Ethylene glycol dimethacrylate | 0 to 24 |
| Diethylene glycol dimethacrylate | 0 to 24 |
| Triethylene glycol dimethacrylate | 0 to 24 |
| Polyethylene glycol dimethacrylate | 0 to 24 |
| Barium glass | 0 to 25 |
| Lithium aluminum silicate | 0 to 85 |
| Flint silica | to 8.5 |
| Borosilicate glass | 0 to 85 |
| Fumed synthetic silica | 0 to 52 |
| Strontium glass | 0 to 85 |
| Quartz | 0 to 85 |
| Titanium dioxide | 0 to 0.13 |
| Tinting agents (e.g., iron oxides) | 0 to 4 |
| A-174 Silane | 0.05 to 1.25 |
| Exciplex-forming photoinitiators | 0.7 to 3.70 |
| Glacial acetic acid | 0.004 to 0.02 |

Powder

| Ingredients | Percent by Weight |
|---|---|
| Barium glass | 0 to 30 |
| Lithium aluminum silicate | 0 to 99.65 |
| Flint silica | 0 to 10 |
| Borosilicate glass | 0 to 99.65 |
| Fumed synthetic silica | 0 to 99.65 |
| Strontium glass | 0 to 99.65 |
| Titanium dioxide | 0 to 0.15 |
| Tinting agent (e.g., iron oxides) | 0 to 5 |
| A-174 silane | 0 to 6.0 |
| Peroxide curing agent (e.g. benzoyl peroxide) | 0.30 to 10 |
| Glacial acetic acid | 0.02 to 0.17 |

EXAMPLE 21

Paste-Powder System

Paste

| Ingredients | Percentage by Weight |
|---|---|
| Ethoxylated bisphenol-A-dimethacrylate | 63.40% |
| 2,3-Bornanedione | 0.056% |
| Ethyl-4-dimethylamino benzoate | 3.1% |
| Fumed silica | 16.05% |
| Barium glass | 16.59% |
| Titanium dioxide | 00.05% |
| Yellow iron oxide | 00.16% |
| Butylated hydroxytoluene | 0.005% |
| Glacial acetic acid | 0.004% |
| 2-Hydroxy-4-methoxy benzophenone | 0.585% |

Powder

| Ingredients | Percentage by Weight |
|---|---|
| Fumed silica | 86.07% |
| Benzoyl peroxide | 8.60% |
| A-174 silane | 5.16% |
| Acetic acid | 0.17% |

When a small amount (10% by weight) of the powder is added to the paste, the resulting heavy paste has a working time of over 20 minutes. When so mixed and exposed to the Visar curing light for 30 seconds, the depth of cure measured at least 4.50 mm. Diametral tensile strength was 5000 psi.

EXAMPLE 22

Paste-Powder System

Paste

| Ingredients | Percentage by Weight |
|---|---|
| Bis-GMA | 9.74% |
| Triethylene glycol dimethacrylate | 6.49% |
| 2,3-Bornanedione | 0.03% |
| Ethyl-4-dimethylamino benzoate | 0.76% |
| Barium glass | 24.52% |
| Lithium aluminum silicate | 57.21% |
| A-174 silane | 1.23% |
| Glacial acetic acid | 0.02% |

Powder

| Ingredients | Percentage by Weight |
|---|---|
| Barium glass | 29.05% |
| Lithium aluminum silicate | 67.78% |
| A-174 silane | 1.45% |

| Ingredients | Percentage by Weight |
| --- | --- |
| Benzoyl peroxide | 1.696% |
| Glacial acetic acid | 0.024% |

The paste and powder are mixed at a weight ratio of 100:5, paste:powder. When so mixed and exposed to a Visar curing unit for 30 seconds, the depth of cure was 5.40 mm. The time to obtain a 12 mm cure was 25 minutes. The diametral tensile strength was 7090 psi.

EXAMPLE 23

Paste-Powder System

Paste

| Ingredients | Percentage by Weight |
| --- | --- |
| Ethoxylated bisphenol-A-dimethacrylate | 12.98% |
| Triethylene glycol dimethacrylate | 3.25% |
| 2,3-Bornanedione | 0.03% |
| Ethyl-4-dimethylamino benzoate | 0.76% |
| Barium glass | 24.52% |
| Lithium aluminum silicate | 57.21% |
| A-174 silane | 1.23% |
| Glacial acetic acid | 0.02% |

Powder

| Ingredients | Percentage by Weight |
| --- | --- |
| Barium glass | 29.05% |
| Lithium aluminum silicate | 67.78% |
| A-174 silane | 1.45% |
| Benzoyl peroxide | 1.696% |
| Glacial acetic acid | 0.024% |

The paste and powder are mixed together at a weight ratio of 100:5, paste:powder. When so mixed and exposed to the output from a Visar curing unit for 30 seconds, the depth of cure was 5.15 mm. The time to a 12 mm cure was 35 minutes. The diametral tensile strength was 5250 psi.

EXAMPLE 24

Paste-Powder System

Paste

| Ingredients | Percentage by Weight |
| --- | --- |
| Ethoxylated bisphenol-A-dimethacrylate | 16.07% |
| 2-Isopropyl thioxanthone | 0.03% |
| Ethyl-4-dimethylamino benzoate | 1.49% |
| Fumed silica | 0.90% |
| Lithium aluminum silicate | 56.204% |
| Barium glass | 24.087% |
| A-174 silane | 1.2% |
| Glacial acetic acid | 0.019% |

Powder

| Ingredients | Percentage by Weight |
| --- | --- |
| Fumed silica (pre-coated with silane) | 95.00% |
| Benzoyl peroxide | 5.00% |

When a small amount (10% by weight) of the powder is added to the paste, the resulting heavy paste has a working time of over 20 minutes. When exposed to the Visar curing light for 30 seconds, the depth of cure measured at least 4.97 mm, the limit of the test fixture used, when measured ten minutes later. Diametral tensile strength was 5240 psi.

EXAMPLE 25

Paste-Powder System

Both the paste and powder were as in Example 24, but a smaller amount (5% by weight) of the powder was added to the paste. The resulting thick paste had a working time of about 30 minutes in ordinary room light. When exposed to a Visar light for 30 seconds, the depth of cure was at least 4.97 mm, that being the limit of the test apparatus used. Diametral tensile strength is 4960 psi.

EXAMPLE 26

Paste-Powder System

Paste

| Ingredients | Percentage by Weight |
| --- | --- |
| Bis-GMA | 9.74% |
| Triethylene glycol dimethacrylate | 6.49% |
| 2-Isopropyl thioxanthone | 0.029% |
| Ethyl-4-dimethylamino benzoate | 1.477% |
| Lithium aluminum silicate | 56.724 |
| Barium glass | 24.310% |
| A-174 silane | 1.21% |
| Glacial acetic acid | 0.02% |

Powder

| Ingredients | Percentage by Weight |
| --- | --- |
| Lithium aluminum silicate | 68.228% |
| Barium glass | 29.558% |
| Benzoyl peroxide | 0.74% |
| A-174 silane | 1.45% |
| Glacial acetic acid | 0.024% |

Thepaste and powder are mixed at a weight ratio of 100:5, paste:powder. When exposed to a Visar II curing unit for 10 seconds, the depth of cure was 4.97 mm. The time to a 12 mm cure was 18 minutes. The diametral tensile strength was 5225 psi.

EXAMPLE 27

Paste-Powder System

Paste

| Ingredients | Percentage by Weight |
| --- | --- |
| Ethoxylated bisphenol-A-dimethacrylate | 12.98% |

-continued

| Ingredients | Percentage by Weight |
|---|---|
| Triethylene glycol dimethacrylate | 3.25% |
| 2-Isopropyl thioxanthone | 0.029% |
| Ethyl-4-dimethylamino benzoate | 1.477% |
| Lithium aluminum silicate | 56.724% |
| Barium glass | 24.310% |
| A-174 silane | 1.21% |
| Glacial acetic acid | 0.02% |

Powder

| Ingredients | Percentage by Weight |
|---|---|
| Lithium aluminum silicate | 68.758% |
| Barium glass | 29.468 |
| Benzoyl peroxide | 0.3% |
| A-174 silane | 1.45% |
| Glacial acetic acid | 0.024% |

The paste and powder are mixed at a weight ratio of 100:5, paste:powder. When exposed to a Visar II curing unit for 30 seconds, the depth of cure was 4.50 mm. The time to a 12 mm cure was 25 minutes. The diametral tensile strength was 5250 psi.

Gel-Powder Systems

Using powder like that used in the powder-liquid system but employing a gel instead of a liquid, a general formulation for these systems may be as follows:

Gel

| Ingredients | Percentage by Weight |
|---|---|
| Resin | 49 to 80.4 |
| Filler | 49 to 10.3 |
| A-174 silane | 0 to 1.25 |
| Exciplex-forming photoinitiator | 2 to 8 |
| Glacial acetic acid | 0 to 0.05 |

Powder

| Ingredients | Percentage by Weight |
|---|---|
| Filler | 99.95 to 93.786 |
| A-174 silane | 0 to 1.50 |
| Peroxide | 0.05 to 4.69 |
| Glacial acetic acid | 0 to 0.024 |

The mixture may vary from about one part of powder to twenty parts of gel to about three parts of powder to one part of gel.

More specifically, while adhering to the general formulation above, the system may use individual ingredients as follows:

Gel

| Ingredients | Percent by Weight |
|---|---|
| Bis-GMA | 0 to 72 |
| Ethoxylated bisphenol-A-dimethacrylate | 0 to 90 |
| Ethylene glycol dimethacrylate | 0 to 54 |
| Diethylene glycol dimethacrylate | 0 to 54 |
| Triethylene glycol dimethacrylate | 0 to 54 |
| Polyethylene glycol dimethacrylate | 0 to 54 |
| Barium glass | 0 to 15 |
| Lithium aluminum silicate | 0 to 50 |
| Flint silica | to 5. |
| Borosilicate glass | 0 to 50 |
| Fumed synthetic silica | 0 to 50 |
| Strontium glass | 0 to 50 |
| Quartz | 0 to 50 |
| Titanium dioxide | 0 to 1 |
| Tinting agents (e.g., iron oxides) | 0 to 5 |
| A-174 Silane | 0 to 1.25 |
| Exciplex-forming photoinitiators | 2 to 8 |
| Glacial Acetic acid | 0 to 0.05 |

Powder

| Ingredients | Percent by Weight |
|---|---|
| Barium glass | 0 to 30 |
| Lithium aluminum silicate | 0 to 99.95 |
| Flint silica | 0 to 10 |
| Borosilicate glass | 0 to 99.95 |
| Fumed synthetic silica | 0 to 99.95 |
| Strontium glass | 0 to 99.95 |
| Titanium dioxide | 0 to 1.50 |
| Tinting agent (e.g., iron oxides) | 0 to 5 |
| A-174 silane | 0 to 1.50 |
| Peroxide curing agent (e.g., benzoyl peroxide) | 0.05 to 4.09 |
| Glacial acetic acid | 0 to 0.024 |

EXAMPLE 28

Gel-Powder System

Gel

| Ingredients | Percentage by Weight |
|---|---|
| Ethoxylated bisphenol-A-dimethacrylate | 76.40% |
| 2,3-Bornanedione | 0.06% |
| Ethyl-4-dimethylamino benzoate | 2.28% |
| Fumed silica | 8.30% |
| Barium glass | 3.831% |
| Lithium aluminum silicate | 8.938% |
| A-174 silane | 0.188% |
| Glacial acetic acid | 0.003% |

Powder

The powder is the same as that of Example 23. The powder and gel are mixed together in a weight ratio of 3:1, powder to gel. When exposed to a visible light dental curing unit for 30 seconds, the material cured to a depth of 4.90 mm. Under normal room fluorescent lighting, the paste had a workable time of approximately 35 minutes. The diametral tensile strength was 5800 psi.

EXAMPLE 29

Gel-Powder System

Gel

| Ingredients | Percentage by Weight |
|---|---|
| Ethoxylated bisphenol-A-dimethacrylate | 76.34% |
| 2,3-Bornanedione | 0.14% |

| Ingredients | Percentage by Weight |
| --- | --- |
| Ethyl-4-dimethylamino benzoate | 2.28% |
| Fumed silica | 21.24% |

Powder

The powder is the same as that used in example 23. The powder and gel are mixed in a ratio of 3:1, powder to gel. When, exposed to a visible light dental curing unit 30 seconds, the material cured to a depth of 5.40 mm. Under normal fluorescent lighting, the paste has a workable time of 25 minutes. The diametral tensile strength was 7090 psi.

EXAMPLE 30

Gel-Powder System

Gel

| Ingredients | Percentage by Weight |
| --- | --- |
| Ethoxylated bisphenol-A-dimethacrylate | 76.40% |
| 2-Isopropylthioxanthone | 0.06% |
| Ethyl-4-dimethylamino benzoate | 6.90% |
| Fumed silica | 8.30% |
| Barium glass | 2.465% |
| Lithium aluminum silicate | 5.752% |
| A-174 silane | 0.121% |
| Glacial acetic acid | 0.002% |

Powder

The powder may be the powder of Example 2 or that of Example 11.

Preferably, the peroxide and silane are again deposited on the powdered glass and silicates as by dissolving the peroxide and the silane in a suitable solvent, such as methylene chloride, chloroform, ether, or acetone, making a slurry with the powder, and then stripping the solvent.

The powder and gel are mixed together in weight ratios of from about 1:20 to 3:1, powder to gel. Mixing, working, and cure time are like those from Examples 2 and 11.

EXAMPLE 31

Gel-Powder System

Gel

| Ingredients | Percentage by Weight |
| --- | --- |
| Ethoxylated bisphenol-A-dimethacrylate | 76.34% |
| 2-Isopropylthioxanthone | 0.14% |
| Ethyl-4-dimethylamino benzoate | 6.90% |
| Fumed silica | 16.62% |

Powder

The powder may be that shown in either of Example 2 or Example 11.

EXAMPLE 32

Gel-Powder System

The gel is as in Example 30, and the powder is as in Example 2.

Here they are mixed at a weight ratio of 2:1, powder:gel. The working time under room lights is 20 minutes. The depth of cure after 30 seconds Visar light exposure was 3.50 mm. The length of time to a 12 mm cure was 18 minutes. The diametral tensile strength was 4975 psi.

EXAMPLE 33

Gel-Powder System

The gel is as in Example 31.
The powder is as follows:

| Ingredients | Percentage by Weight |
| --- | --- |
| Fumed synthetic silica | 93.90% |
| A-174 silane | 1.41% |
| Peroxide curing agent | 4.69% |

The gel and powder are mixed at a weight ratio of 20:1.

The gel-powder working time is 25 minutes under room lights. The depth of cure after 30 seconds exposure to Visar curing light was 3.35 mm. The length of time to a 12 mm cure depth was 20 minutes. The diametral tensile strength was 4400 psi.

This restorative system may be used in the repair of fractured porcelain material, natural teeth, or in any other intra-oral situation where a resin material is desired to replace or simulate tooth structure that is capable of being polymerized by visible light and having the process continue after the light is removed.

Also, this restorative system, which is essentially a light-cured system, achieves uniform polymerization within thirty minutes to one hour after insertion in the patient's mouth, even though variable amounts of light be exposed to the polymerizing resin.

This system eliminates the color changes that tend to occur when certain resins mixed with curing resins are exposed to ultra-violet or visible light.

To those skilled in the art to which this invention relates, many changes in construction and widely differing embodiments and applications of the invention will suggest themselves without departing from the spirit and scope of the invention. The disclosures and the descriptions herein are purely illustrative and are not intended to be in any sense limiting.

What is claimed is:

1. A filled-resin composition useful for porcelain repair and as a dental composite and therefore made up of non-toxic materials, comprising:

a methacrylate functional resin usable in dental composites, powdered filler-colorant therein, at least one photoinitiator for said resin in an amount sufficient to initiate polymerization and complete it in depth within about half a minute when exposed to a visible-light output of at least 5,000 foot candles, while insufficient to result in curing when exposed for thirty minutes, to the light normally present in a lighted dental operatory, so as to afford a dentist adequate time for mixing, changing the coloring, and placement in a patient's mouth, said photoinitiator being an exciplex of (1) a carbocyclic ketone or acetal and (2) either ethyl-4-dimethyl amino benzoate or ethyl-2-dimethyl amino benzoate, and at least one accelerator-free peroxide curing agent for said resin in an effective amount for slowly completing polymerization within about an hour of any portion of said resin not receiving sufficient light to effectuate complete cure before then.

2. The composition of claim 1 wherein said peroxide curing agent is benzoyl peroxide.

3. The composition of claim 1 wherein each said photoinitiator is an exciplex chosen from the group consising of:
2,3-Bornanedione with ethyl-4-dimethyl amino benzoate
2,3-Bornanedione with ethyl-2-dimethyl amino benzoate
Benzil with ethyl-4-dimethyl amino benzoate
Benzil with ethyl-2-dimethyl amino benzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan-1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophenone with ethyl-2-dimethyl amino benzoate
Benzoin methyl ether with ethyl-4-dimethyl amino benzoate
Benzoin methyl ether with ethyl-2-dimethyl amino benzoate.

4. The composition of claim 1 wherein the resin is at least one resin chosen from the group consisting of ethoxylated bisphenol-A-dimethacrylate, Bis-GMA, and an adduct of 2,2'-propane bis[3-(4-phenoxy)-1,2-hydroxy propane-1 methacrylate] and mono- or di-isocyanate.

5. The composition of claim 1, wherein said peroxide curing agent is benzoyl peroxide,
the carbocyclic ingredient is 2,3-bornanedione, and
said benzoate is ethyl-4-dimethyl amino benzoate.

6. A two-part system for making a filled methacrylate-functional resin composition by mixture of the two parts, comprising:
first part: dental-type filler powder with an accelerator-free peroxide curing agent for said resin,
second part: dental-type methacrylate-functional resin with photoinitiator therefor,
said photoinitiator being an exciplex of (1) a carbocyclic ketone or acetal and (2) either ethyl-4-dimethyl amino benzoate or ethyl-2-dimethyl amino benzoate, in an amount sufficient to initiate polymerization and complete it within about half a minute after the first part and second parts are mixed and then exposed during cure to at least 5,000 foot candles visible light, while insufficient to result in curing, when exposed, for thirty minutes in a lighted dental operatory, so as to afford a dentist adequate time for mixing, adjusting, and placement in a patient's mouth,
said peroxide curing agent being present in an amount effective to complete cure of any resin portion not sufficiently exposed to said light within about an hour.

7. The system of claim 6 wherein the first part is in the form of a powder.

8. The system of claim 7 wherein the second part is in the form of a liquid.

9. The system of claim 8 wherein the powder to liquid weight ratio is from about 1:1 to about 4:1.

10. The system of claim 7 wherein the second part is in the form of a gel and also contains some filler.

11. The system of claim 10 wherein the powder-gel weight ratio is from about 1:20 to about 3:1.

12. The system of claim 6 wherein both the first and second parts are in paste form, both containing substantial amounts of filler.

13. The system of claim 12 wherein the first and second parts are so formulated to enable mixture of equal parts by weight at the time of use.

14. The system of claim 6 wherein the resin is at least one resin chosen from the group consisting of ethoxylated bisphenol-A-dimethacrylate and an adduct of 2,2'-propane bis[3-(4-phenoxy)-1,2-hydroxy propane-1 methacrylate] and mono- or di-isocyanate.

15. The system of claim 14 wherein said peroxide curing agent is benzoyl peroxide.

16. The system of claim 14 wherein each said photoinitiator is chosen from the group consisting of:
2,3-Bornanedione with ethyl-4-dimethyl amino benzoate
2,3-Bornanedione with ethyl-2-dimethyl amino benzoate
Benzil with ethyl-4-dimethylaminobenzoate
Benzil with ethyl-2-dimethylaminobenzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan-1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophenone with ethyl-2-dimethyl amino benzoate
Benzoin methyl ether with ethyl-4-dimethyl amino benzoate
Benzoin methyl ether with ethyl-2-dimethyl amino benzoate.

17. The system of claim 6, wherein said peroxide curing agent is benzoyl peroxide,
the carbocyclic ingredient is 2,3-bornanedione, and
said benzoate is ethyl-4-dimethyl amino benzoate.

18. A porcelain-repair and dental composite composition of matter consisting essentially of a powder component consisting essentially by weight of:
   Dental filler-colorant material: 99.85% to 97.7%
   Gamma-methacryloxy propyl trimethoxy silane: 0.10% to 1.55%,
   Peroxide curing agent: 0.05% to 0.70%,
   Glacial acetic acid: 0 to 0.05%,
and a liquid component consisting essentially, by weight of:
   a methacrylate-functional resin suitable for use in dental composites: 99.3% to 82%,
   exciplex-forming photoinitiator for said resin: 0.7% to 18%,
said powder and resin being mixed together in a weight ratio between 1:1 and 4:1 of powder to liquid, said photoinitiator being at least one item chosen from the group consisting of:
   2,3-Bornanedione with ethyl-4-dimethyl amino benzoate
   2,3-Bornanedione with ethyl-2-dimethyl amino benzoate
   Benzil with ethyl-4-dimethyl amino benzoate
   Benzil with ethyl-2-dimethylaminobenzoate
   2-Isopropyl thioxanthone with ethyl-4-dimethyl amino benzoate
   2-Isopropyl thioxanthone with ethyl-2-dimethyl amino benzoate
   Dibenzyl ketone with ethyl-4-dimethyl amino benzoate
   Dibenzyl ketone with ethyl-2-dimethyl amino benzoate
   2-Hydroxy-2-methyl-1-phenyl-propan-1-one with ethyl-2-dimethyl amino benzoate
   2-Hydroxy-2-methyl-1-phenyl-propan-1-one with ethyl-4-dimethyl amino benzoate
   Benzil dimethyl acetal with ethyl-4-dimethyl amino benzoate
   Benzil dimethyl acetal with ethyl-2-dimethyl amino benzoate
   Dimethoxy acetophenone with ethyl-4-dimethyl amino benzoate
   Dimethoxy acetophenone with ethyl-2-dimethyl amino benzoate
   Benzoin methyl ether with ethyl-4-dimethyl amino benzoate
   Benzoin methyl ether with ethyl-2-dimethyl amino benzoate.

19. The porcelain-repair and dental composite composition of matter of claim 18 wherein:
said filler-colorant consists essentially by weight of ingredients totaling as in claim 16 and selected from the group consisting of:
   Barium glass: 0% to 30%,
   Lithium aluminum silicate: 0% to 99.85%,
   Flint silica: 0% to 10%,
   Borosilicate glass: 0% to 99.85%,
   Fumed synthetic silica: 0% to 99.85%,
   Quartz: 0% to 99.85%,
   Custer feldspar: 0% to 10%,
said powder component also including, in addition to the silane, the peroxide curing agent, and the glacial acetic acid:
   Titanium dioxide: 0% to 0.15%,
   Metal salts: 0% to 5.00%,
said methacrylate-functional resin totaling as in claim 16 and consisting essentially by weight of ingredients:
   Bis-GMA: 0% to 80%,
   Ethoxylated bisphenol-A-dimethacrylate: 0% to 99%,
   Ethylene glycol dimethacrylate 0% to 60%,
   Diethylene glycol dimethacrylate 0% to 60%,
   Triethylene glycol dimethacrylate 0% to 60%,
   Polyethylene glycol dimethacrylate 0% to 60%,
   Exciplex forming photoinitiator 0.7% to 18%.

20. The composition of claim 18 wherein said peroxide curing agent is benzoyl peroxide.

21. The composition of claim 18, wherein said peroxide curing agent is benzoyl peroxide, and
   said photoinitiator is an exciplex of 2,3-bornanedione and ethyl-4-dimethyl amino benzoate.

22. A porcelain-repair and dental composite restorative material consisting essentially of:
   (a) a powder component, consisting essentially of a powdered dental filler-colorant, with a powdered peroxide curing agent in an amount between 0.05% and 1% by weight of said powder component, and
   (b) a liquid component, consisting essentially of
      (1) a methacrylate-functional resin suitable for use in dental composites in an amount of 84–96% by weight of said liquid component, and
      (2) a photoinitiator for said resin consisting of an exciplex incorporating as one ingredient either ethyl-4-dimethyl amino benzoate or ethyl-2-dimethyl amino benzoate in an amount of about 0.7 to 10% by weight of said liquid component, the other ingredient being present in an amount of 0.01–8%, by weight of said liquid component, for a total photoinitiator amount by weight of said liquid component of about 0.7 to 18%,
   said other ingredient of said exciplex being a single compound selected from the group consisting of 2,3-bornanedione, 2-isopropyl thioxanthone, dimethoxy acetophenone, benzil dimethyl acetal, and 2-hydroxy-2-methyl-1-phenyl-propan-1-one,
   said powder and liquid components being mixed together just before use in a weight ratio of from 2:1 to 3½ powder to liquid.

23. The restorative material of claim 22 wherein said powder component is selected from the group consisting of barium glass, strontium glass, lithium aluminum silicate, flint silica and mixtures of the members of this group with each others.

24. The restorative material of claim 23 wherein said powder component is a mixture of barium glass, lithium aluminum silicate and flint silica.

25. The restorative material of claim 24, wherein said powder component, by weight of said powder component contains:
   Barium glass: 23–30%,
   Lithium aluminum silicate: 54–70%,
   Flint silica: 1–70%,
   for a total filler content of about 97½ to 99.85%.

26. The restorative material of claim 22 wherein said powder component also contains glacial acetic acid and gamma-methacryloxy propyl trimethoxy silane.

27. The restorative material of claim 26 wherein said glacial acetic acid is present in an amount of about 0.001–0.05%, by weight of said powder component, and said silane is present in an amount of about 1/10 of 1% to about 1½% by weight of said powder component.

28. The restorative material of claim 22 wherein the resin in said liquid component is selected from the group consisting of ethoxylated bisphenol-A-dimethacrylate, bis-GMA, a mixture of ethoxylated bisphenol-A-dimethacrylate and an ethylene glycol dimethacrylate, and a mixture of bis-GMA and an ethylene glycol dimethacrylate.

29. The restorative material of claim 28 wherein said resin is ethoxylated bisphenol-A-dimethacrylate in an amount of about 82 to 99.3% by weight of said liquid component.

30. The restorative material of claim 28 wherein said resin is a mixture, by weight of said liquid component, of about 60–84% ethoxylated bisphenol-A-dimethacrylate and about 40–16% triethylene glycol dimethacrylate.

31. The restorative material of claim 28 wherein said resin is a mixture, by weight of said liquid component of about 55% Bis-GMA and about 36% of triethylene glycol dimethacrylate.

32. The restorative material of claim 22, wherein said peroxide curing agent is benzoyl peroxide and said photoinitiator is an exciplex of ethyl-4-dimethyl amino benzoate and 2,3-bornanedione.

33. The restorative material of claim 32 wherein said powder component is a mixture of barium glass and lithium aluminum silicate.

34. The restorative material of claim 22 wherein the amounts by weight of said other ingredient in said liquid component are:
   2,3 Bornanedione: 0.02–0.2%,
   2-Isopropylthioxanthone: 0.02–0.2%,
   Dimethoxy acetophenone: 0.02–8%,
   Benzil dimethyl acetal: 0.02–7%,
   2-hydroxy-2-methyl-1-phenyl propan-1-one: 0.02–8%.

35. The restorative material of claim 22 wherein said liquid component also includes BHT in an amount of about 0.02% by weight of said liquid component.

36. A two-paste system for porcelain and dental restoration, said pastes being mixed together at the time of use in substantially equal amounts by weight,
   both pastes containing methacrylate-functional resin suitable for use in dental components and dental filler material in an amount totaling over 95% thereof by weight of each paste,
   one said paste containing a peroxide curing agent for said resin in an amount of about 0.1% to 1.0% by weight of that paste,
   the other said paste containing an exciplex visible-light-reactive photoinitiator for said resin in an amount of about 1 to 3.5% by weight of that paste, said exciplex including either ethyl-4-dimethyl amino benzoate or ethyl-2-dimethyl amino benzoate, the other ingredient of the exciplex being selected from the group consisting of 2,4 bornanedione in an amount of about 0.06% by weight of the paste containing it and 2-isopropyl thioxanthone in an amount of 0.015%–0.06% of the exciplex-containing paste.

37. The system of claim 36 in which each paste also contains gamma-methacryloxy propyl trimethoxy silane in an amount of about 0.05 to 1.2% by weight of each paste.

38. The system of claim 36 in which at least one of the pastes also contains glacial acetic acid in an amount of at least 0.0015% by weight of that paste.

39. The system of claim 36 wherein said resin is ethoxylated bisphenol-A-dimethacrylate.

40. The system of claim 36 wherein said resin is present in the peroxide-containing paste in an amount of about 14–40% and is present in the exciplex-containing paste in an amount of 14–36%.

41. The system of claim 36 wherein said filler is chosen from (a) the group consisting of strontium glass and a mixture of barium glass with lithium aluminum silicate, and also includes fumed silica.

42. The system of claim 41 wherein the filler comprises, by weight of each paste about 1% of fumed silica and about 80% of strontium glass.

43. The system of claim 41 wherein the filler comprises, by weight of each paste, about 1% of fumed silica, about 23–25% of barium glass, and about 54–58% of lithium aluminum silicate.

44. A paste-powder system for use in dental and porcelain restoration, the paste and powder being mixed at the time of use at a ratio of paste to powder of about 10:1 to 20:1,
   said paste comprising the mixture of methacrylate-functional dental resin and powdered dental filler in a total amount of about 96–99% by weight of the paste and having an exciplex, visual-light reactive photoinitiator in a total amount of about 0.7–10% by weight of the paste,
   said exciplex being made up of
   (a) either 2,3-bornanedione or 2-isopropyl thioxanthone in an amount of about 0.03% to 0.06% by weight of said paste and,
   (b) either ethyl-4-dimethyl amino benzoate or ethyl-2-dimethyl amino benzoate in an amount of about 0.75 to 3.25% by weight of said paste,
   said powder consisting essentially of a dental filler and a peroxide curing agent for the resin in an amount of about 0.3%–9% of the powder.

45. The system of claim 44 wherein said resin is selected from the group consisting of ethoxylated bisphenol-A-dimethacrylate, a mixture thereof with an ethylene glycol dimethacrylate, and a mixture of bis-GMA with an ethylene glycol dimethacrylate.

46. The system of claim 45 wherein the resin is from 16–64% ethoxylated bisphenol-A-dimethacrylate, by weight of said paste.

47. The system of claim 45 wherein the resin is a mixture of about 13% ethoxylated bisphenol-A-dimethacrylate and about 3¼% of triethylene glycol dimethacrylate, both by weight of said resin.

48. The system of claim 45 wherein the resin is a mixture of about 10% bis-GMA and about 6½% triethylene glycol dimethacrylate, both by weight of said resin.

49. The system of claim 44 wherein the filler is fumed silica.

50. The system of claim 44 wherein the filler is a mixture of lithium aluminum silicate and barium glass.

51. The system of claim 44 wherein at least the powder contains gamma-methacryloxy propyl trimethoxy silane, in an amount of about 1.25 to 5.25% by weight of its component.

52. The system of claim 44 wherein at least the powder contains glacial acetic acid in an amount of about 0.02 to 0.2% by weight of its component.

53. A gel-powder system for use in dental and porcelain restoration, the gel and powder being mixed at the time of use for cure by visible light, in a ratio of about 20:1 to 1:3 of gel to powder,
   the gel consisting essentially of about ¾ methacrylate-functional dental resin and about ¼ dental filler to a total amount of about 93–98% by weight of said gel and an exciplex, visible-light-reactive photoinitiator having two ingredients, one of which is either ethyl-4-dimethyl amino benzoate or ethyl-2- dimethyl amino benzoate, in a total amount of about 2% to 7% by weight of the gel,
said powder consisting essentially of a dental filler and an accelerator-free peroxide curing agent for said resin in an amount of about 0.1%–10% by weight of said powder,
said exciplex being made up of
(a) either 2,3-bornanedione or 2-isopropyl thioxanthone in an amount of about 0.005 to 0.15% by weight of said gel and,
(b) either ethyl-4-dimethyl amino benzoate or ethyl-2-dimethyl amino benzoate in an amount of about 2.0 to 8% by weight of said gel.

54. The system of claim 53 wherein said resin is ethoxylated bisphenol-A-dimethacrylate.

55. The system of claim 53 wherein said filler for the powder component is selected from the group consisting of barium glass, lithium aluminum silicate, flint silica and mixtures of the members of this group with each others.

56. The system of claim 53 wherein said filler for the powder component is a mixture of barium glass, lithium aluminum silicate and flint silica.

57. The system of claim 53 wherein said filler for the powder component contains, by weight of the powder, 26–30% barium glass, 62–70% lithium aluminum silicate and 1–10% flint silica.

58. The system of claim 53 wherein said filler for the gel component is fumed silica.

59. The system of claim 53 wherein said filler for the gel component is a mixture of barium glass and lithium aluminum silicate.

60. The system of claim 53 wherein said filler for the gel component comprises, by weight of the gel, about 2–5% barium glass, about 5–10% lithium aluminum silicate and about 7–10% fumed silica.

61. The system of claim 53 wherein at least the powder component contains gamma-methacryloxy propyl trimethoxy silane, in an amount of about 0.05 to 2.0% by weight of its component.

62. The system of claim 53 wherein at least the powder component contains glacial acetic acid, in an amount of about 0.01 to 0.05% by weight of its component.

63. A method for repairing porcelain or teeth, comprising
mixing together under ordinary indoor lighting conditions, a methacrylate functional resin usable in dental composites, powdered dental filler-colorant, at least one photoinitiator for said resin in an amount sufficient to initiate polymerization and complete it in depth within about half a minute when exposed to a visible-light output of at least 5000 foot-candles, said photoinitiator being an exciplex of (1) a carbocyclic ketone or acetal and (2) either ethyl-4-dimethyl amino benzoate or ethyl-2-dimethyl amino benzoate, and at least one accelerator-free peroxide curing agent for said resin in an effective amount for completing polymerization within about an hour of any portion of said resin not receiving sufficient light to effect complete cure before then,
emplacing the mixture within a few minutes of the mixing, and
curing at least a substantial portion of the emplaced mixture in situ for one half-minute under intense visual-light illumination of at least 5000 foot-candles, any resin then uncured by light being cured within about another hour by said peroxide curing agent.

64. The method of claim 63 wherein the resin is at least one resin chosen from the group consisting of ethoxylated bisphenol-A-dimethacrylate, bis-GMA, and an adduct of 2,2'-propane bis[3-(4-phenoxy)-1,2-hydroxy propane-1 methacrylate] and mono- or di-isocyanate.

65. The method of claim 63 wherein said peroxide curing agent is benzoyl peroxide.

66. The method of claim 63 wherein each said photoinitiator is an exciplex chosen from the group consisting of:
2,3-Bornanedione with ethyl-4-dimethyl amino benzoate
2,3-Bornanedione with ethyl-2-dimethyl amino benzoate
Benzil with ethyl-4-dimethyl amino benzoate
Benzil with ethyl-2-dimethyl amino benzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan-1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophenone with ethyl-2-dimethyl amino benzoate
Benzoin methyl ester with ethyl-4-dimethyl amino benzoate
Benzoin methyl ether with ethyl-2-dimethyl amino benzoate.

67. A method for preparing a storable filled-resin composition for porcelain repair and as a dental composite, comprising:
mixing a methacrylate functional resin usable in dental composites with at least one photoinitiator for said resin, in an amount sufficient to initiate polymerization and complete it in depth within about half a minute when exposed to a visible-light output of at least 5000 foot-candles, said photoinitiator being an exciplex of (1) a carbocyclic ketone or acetal and (2) either ethyl-4-dimethyl amino benzoate or ethyl-2-dimethyl amino benzoate,
storing the resin-photoinitiator mixture in an opaque container,
coating a powdered dental filler-colorant with at least one accelerator-free peroxide curing agent for said resin in an effective amount substantially less than stoichiometric, and sufficient to effect completion of polymerization within about an hour of any portion of said resin not receiving sufficient light durng said half a minute, and
storing said filler-colorant and peroxide mixture,
whereby at the time of use said resin-photoinitiator mixture can be mixed with said peroxide-coated filler-colorant under ordinary indoor illumination.

68. A method for repairing porcelain or teeth, comprising preparing under ordinary indoor lighting conditions, a liquid mixture consisting essentially of a methacrylate functional resin usable in dental composites, and at least one photoinitiator for said resin in an amount sufficient to initiate polymerization and complete it in depth within about half a minute when exposed to a visible-light output of at least 5000 foot-candles, said photoinitiator being an exciplex of (1) a carbocyclic ketone or acetal and (2) either ethyl-4-dimethyl amino benzoate or ethyl-2-dimethyl amino benzoate, preparing under ordinary indoor lighting conditions a powdered mixture of powdered dental filler-colorant and at least one accelerator-free peroxide curing agent for said resin in an effective amount for completing polymerization within about an hour of any portion of said resin not receiving sufficient light to effect complete cure before then, mixing said powder mixture and said liquid mixture together under ordinary indoor lighting conditions in a powder to liquid ratios of about 1:1 to 4:1 just prior to use to provide a repair mixture, emplacing the repair mixture within a few minutes of the mixing, and curing at least a substantial portion of the emplaced mixture in situ for one half-minute under intense visual-light illumination of at least 5000 foot-candles, any resin then uncured by light being curred within the next half hour by said peroxide curing agent.

69. The method of claim 68 wherein said peroxide curing agent is benzoyl peroxide.

70. The method of claim 68 wherein each said photoinitiator is an exciplex chosen from the group consisting of:

2,3-Bornanedione with ethyl-4-dimethyl amino benzoate 2,3-Bornanedione with ethyl-2-dimethyl amino benzoate Benzil with ethyl-4-dimethyl amino benzoate Benzil with ethyl-2-dimethyl amino benzoate 2-Isopropyl thioxanthone with ethyl 4-dimethyl amino benzoate 2-Isopropyl thioxanthone with ethyl-2-dimethyl amino benzoate Dibenzyl ketone with ethyl-4-dimethyl amino benzoate Dibenzyl ketone with ethyl-2-dimethyl amino benzoate 2-Hydroxy-2-methyl-1-phenyl-propan-1-one with ethyl-2-dimethyl amino benzoate 2-Hydroxy-2-methyl-1-phenyl-propan-1-one with ethyl-4-dimethyl amino benzoate Benzil dimethyl acetal with ethyl-4-dimethyl amino benzoate Benzil dimethyl acetal with ethyl-2-dimethyl amino benzoate Dimethoxy acetophenone with ethyl-4-dimethyl amino benzoate Dimethoxy acetophenone with ethyl-2-dimethyl amino benzoate Benzoin methyl ether with ethyl-4-dimethyl amino benzoate Benzoin methyl ether with ethyl-2-dimethyl amino benzoate.

71. The method of claim 69 wherein said exciplex constitutes about 0.7% to about 18% by weight of said liquid mixture and said peroxide constitutes about 0.1 to about 0.8% of said powder mixture.

72. The method of claim 68 having the step in between preparing and mixing of storing said powder in a container and of storing said liquid in an opaque container.

73. A method for repairing porcelain or teeth, comprising:

providing under ordinary indoor lighting conditions first paste consisting essentially of a methacrylate functional resin usable in dental composites, a powdered dental filler-colorant, and at least one photoinitiator for said resin in an amount sufficient to initiate polymerization and complete it in depth within about half a minute when exposed to a visible-light output of at least 5000 foot-candles, said photoinitiator being n exciplex of (1) a carbocyclic ketone or acetal and (2) either ethyl-4-dimethyl amino benzoate or ethyl-2-dimethyl amino benzoate, providing under ordinary indoor lighting conditions a second paste consisting essentially of a methacrylate functional resin usable in dental composites, a powdered dental filler colorant, and at least one accelerator-free peroxide curing agent for said resin in an effective amount for completing polymerization within about an hour of any portion of said resin not receiving sufficient light to effectuate complete cure before then, mixing under ordinary indoor lighting conditions said first and second pastes in approximately the same amount of each, to form a paste mixture, emplacing the paste mixture within a few minutes of the mixing, and curing at least a substantial portion of the emplaced mixture in situ for one half-minute under intense visual-light illumination of at least 5000 foot-candles, any resin then uncured by light being cured within about an hour thereafter by said peroxide curing agent.

74. The method of claim 73 wherein said peroxide curing agent is benzoyl peroxide.

75. The method of claim 73 wherein each said photoinitiator is an exciplex chosen from the group consisting of:

2,3-Bornanedione with ethyl-4-dimethyl amino benzoate 2,3-Bornanedione with ethyl-2-dimethyl amino benzoate Benzil with ethyl-4-dimethyl amino benzoate Benzil with ethyl-2-dimethyl amino benzoate 2-Isopropyl thioxanthone with ethyl-4-dimethyl amino benzoate 2-Isopropyl thioxanthone with ethyl-2-dimethyl amino benzoate Dibenzyl ketone with ethyl-4-dimethyl amino benzoate Dibenzyl ketone with ethyl-2-dimethyl amino benzoate 2-Hydroxy-2-methyl-1-phenyl-propan-1-one with ethyl-2-dimethyl amino benzoate 2-Hydroxy-2-methyl-1-phenyl-propan-1-one with ethyl-4-dimethyl amino benzoate Benzil dimethyl acetal with ethyl-4-dimethyl amino benzoate Benzil dimethyl acetal with ethyl-2-dimethyl amino benzoate Dimethoxy acetophenone with ethyl-4-dimethyl amino benzoate Dimethoxy acetophenone with ethyl-2-dimethyl amino benzoate Benzoin methyl ether with ethyl-4-dimethyl amino benzoate Benzoin methyl ether with ethyl-2-dimethyl amino benzoate.

76. The method of claim 73 wherein said first paste, at least, is prepared long in advance and comprising the step of storing said first paste in an opaque container until said mixing step.

77. The method of claim 73 in which said exciplex constitutes about 1 to 4% by weight of said first paste and said peroxide constitutes about 0.1 to 1.0% by weight of said second paste.

78. A method for repairing porcelain or teeth, comprising:
mixing together under ordinary indoor lighting conditions a paste consisting essentially of a methacrylate functional resin usable in dental composites, powdered dental filler-colorant, at least one photoinitiator for said resin in an amount sufficient to initiate polymerization and complete it in depth within about half a minute when exposed to a visible-light output of at least 5000 foot-candles, said photoinitiator being an exciplex of (1) a carbocyclic ketone or acetal and (2) either ethyl-4-dimethyl amino benzoate or ethyl-2-dimethyl amino benzoate,
mixing together under ordinary indoor lighting conditions powder consisting essentially of a powdered dental filler-colorant and at least one accelerator-free peroxide curing agent for said resin in an effective amount for completing polymerization within about one-half hour of any portion of said resin not receiving sufficient light to effective complete cure before then,
mixing together under ordinary indoor lighting conditions, immediately before use, said paste and said powder in a ratio of paste to powder of about 20:1 to 10:1, to form a thick paste,
emplacing the thick paste within a few minutes of the mixing, and
curing at least a substantial portion of the emplaced mixture in situ for one half-minute under intense visual-light illumination of at least 5000 foot-candles, any resin then uncured by light being cured within about an hour thereafter by said peroxide curing agent.

79. The composition of claim 78 wherein said peroxide curing agent is benzoyl peroxide.

80. The composition of claim 78 wherein each said photoinitiator is an exciplex chosen from the group consisting of:
2,3-Bornanedione with ethyl-4-dimethyl amino benzoate
2,3-Bornanedione with ethyl-2-dimethyl amino benzoate
Benzil with ethyl-4-dimethyl amino benzoate
Benzil with ethyl-2-dimethyl amino benzoate
2-Isopropyl thioxanthone with ethyl-4-dimethyl amino benzoate
2-Isopropyl thioxanthone with ethyl-2-dimethyl amino benzoate
Dibenzyl ketone with ethyl-4-dimethyl amino benzoate
Dibenzyl ketone with ethyl-2-dimethyl amino benzoate
2-Hydroxy-2-methyl-1-phenyl-propan-1-one with ethyl-2-dimethyl amino benzoate
2-Hydroxy-2-methyl-1-phenyl-propan-1-one with ethyl-4-dimethyl amino benzoate
Benzil dimethyl acetal with ethyl-4-dimethyl amino benzoate
Benzil dimethyl acetal with ethyl-2-dimethyl amino benzoate
Dimethoxy acetophenone with ethyl-4-dimethyl amino benzoate
Dimethoxy acetophonone with ethyl-2-dimethyl amino benzoate
Benzoin methyl ether with ethyl-4-dimethyl amino benzoate
Benzoin methyl ether with ethyl-2-dimethyl -amino benzoate.

81. The method of claim 78 wherein said mixing of said paste is done well in advance of use including the step of storing said paste in an opaque container prior to said mixing of the powder with the paste.

82. The method of claim 78 wherein said exciplex constitutes about 0.7 to 4% of said paste and said peroxide constitutes about 0.3 to about 10% of said powder.

83. A method for repairing porcelain or teeth, comprising:
mixing together under ordinary indoor lighting conditions,
a gel consisting essentially of about ¾ methacrylate-functional dental resin and about ¼ dental filler to a total amount of about 93 to 97½% by weight of the gel and an exciplex, visible-light-reactive photoinitiator having two ingredients, one of which is either ethyl-4-dimethyl amino benzoate or ethyl-2-dimethyl amino benzoate in an amount of about 2.0 to 7.5% by weight of the gel the other ingredient being either 2,3-bornanedione or 2-isopropyl thioxanthone in an amount of about 0.005 to 0.15% by weight of the gel, in a total amount of about 2% to 8% by weight of the gel,
with a powder consisting essentially of a filler and an accelerator free peroxide curing agent for the resin in an amount of about 0.1-5% by weight of the powder,
in a ratio of about 20:1 to 1:3 of gel to powder,
emplacing the gel-powder mixture within a few minutes of mixing, and
curing at least a substantial portion of the emplaced mixture in situ for one half-minute under intense visual-light illumination of at least 5000 foot-candles, any resin then uncured by light being cured within about an hour thereafter by said peroxide curing agent.

84. The method of claim 83 wherein the resin is ethoxylated bisphenol-A-dimethacrylate.

85. The method of claim 83 wherein the filler for the gel component is fumed silica.

86. The method of claim 83 wherein the filler for the gel component comprises, by weight of the gel, about 2-5% barium glass, about 5-10% lithium aluminum silicate and about 7-10% fumed silica.

87. The method of claim 83 wherein the filler for the powder component is selected from the group consisting of barium glass, lithium aluminum silicate, flint silica and mixtures of the members of this group with each other.

88. The method of claim 83 wherein the filler for the powder component contains, by weight of the powder, 16-30% barium glass, 62-70% lithium aluminum silicate and 1-10% flint silica.

* * * * *